United States Patent [19]

Hilfinger et al.

[11] Patent Number: 6,048,551
[45] Date of Patent: Apr. 11, 2000

[54] MICROSPHERE ENCAPSULATION OF GENE TRANSFER VECTORS

[76] Inventors: John M. Hilfinger, 2578 Easy St., Ann Arbor, Mich. 48104; Beverly L. Davidson, 4004 El Paso Dr.; Steven J. Beer, 25 Lincoln Ave., Apt. 6, both of Iowa City, Iowa 52246; John R. Crison, 1805 N. Franklin Ct., Ann Arbor, Mich. 48103; Gordon L. Amidon, 2079 S. Seventh St., Ann Arbor, Mich. 48109

[21] Appl. No.: 08/824,997

[22] Filed: Mar. 27, 1997

[51] Int. Cl.[7] .............................. A61K 9/50; A61F 2/02; B01J 13/02; B32B 5/16

[52] U.S. Cl. .......................... 424/501; 424/426; 424/502; 264/4.1; 264/4.3; 264/4.33; 264/4.7; 428/402.21

[58] Field of Search ..................................... 424/426, 501, 424/502; 264/4.1, 4.3, 4.33, 4.7; 428/402.21

[56] References Cited

U.S. PATENT DOCUMENTS

| | | | |
|---|---|---|---|
| 4,948,586 | 8/1990 | Bohm et al. | 424/406 |
| 5,160,745 | 11/1992 | DeLuca et al. | 424/487 |
| 5,463,092 | 10/1995 | Hostetler et al. | 554/40 |
| 5,498,421 | 3/1996 | Grinstaff et al. | 424/450 |

OTHER PUBLICATIONS

Barba et al., (1994) Development of anti–tumor immunity following thymidine kinase–mediated killing of experimental brain tumors. *Proc. Natl. Acad. Sci., USA*, 91:4348–4352.

Barr et al. (1995) Strain related variations in adenovirally mediated transgene expression from mouse hepatocytes in vivo . . . *Gene Ther.*, 2:151–155.

Berg et al., (1995) Interleukin–10 is a central regulator of the response to LPS in murine models of endotoxic shock . . . *J. Clin. Invents.*, 96:2339–2347.

Blumberg et al., (1995) The immune system. in *Textbook of Gastroenterology*. Yamada T., Ed. Lippincott EdII, pp. 111–140.

Boviatsis et al., (1994) Gene transfer into experimental brain tumors mediated by adenovirus, herpes simplex virus et al. *Hum. Gene Ther.*, 5:183–191.

Brem et al., (1994) Biodegradable polymers for controlled delivery of chemotherapy with and without radiation therapy . . . *J. Neurosurg.*, 80:282–290.

Brownlee and Cerami (1983) Glycosylated insulin complexed to Concanavalin A. Biochemical basis for a closed–loom insulin . . . *Diabetes*, 32:499–405.

Brownlee and Cerami (1979) A glucose–controlled insulin–delivery system: semisynthetic insulin bound to lectin. *Science*, 209:1190–1191.

Brynes et al., (1995) Adenovirus gene transverse causes inflammation in the brain. *Neuroscience*, 66:1015–1024.

Chen et al., (1994) Gene therapy for brain tumors: regression of experimental gliomas by adenovirus–mediated gene transfer . . . *Proc. Natl. Acad. Sci. USA*, 91:3054–3057.

Cohen et al., (1991) Controlled delivery systems for proteins based on poly(lactic/glycolic acid) microspheres. *Pharm. Res.*, 8:713–720.

Comanelli et al., (1990) Interleukin 1 (IL–1) gene expression, synthesis, and effect of specific IL–1 receptor . . . *J. Clin. Invest.*, 86:972–980.

Cowsar et al., (1985) Poly(lactide–co–glycolid) microcapsules for controlled release of steroids. *Methods Enymol.*, 112:101–116.

(List continued on next page.)

Primary Examiner—Carlos A. Azpuru
Attorney, Agent, or Firm—Kohn & Associates

[57] ABSTRACT

A controlled release delivery system includes a functional gene vector in a biodegradable polymeric microsphere encapsulating the vector. The present invention further provides a method of making a controlled release delivery system by encapsulating the functional gene vector in a biologically degradable polymeric microsphere.

13 Claims, 10 Drawing Sheets

(1 of 10 Drawing Sheet(s) Filed in Color)

OTHER PUBLICATIONS

Culver et al., (1992) In vivo gene transfer with retroviral vector–producer cells for treatment of experimental brain tumors *Science,* 256:1550–1552.

Davidson et al., (1994) Expression of *Escherichia coli* beta–galactosidase and rat HPRT in the CNS of Macaca mulatta . . . *Exp. Neurol.,* 125:258–267.

Davis (1972) Control of diabetes with polyacrylamide implants containing insulin. *Experientia,* 28:348.

Dinarello and Wolff (1993) The role of interleukin–1 in disease. *N. Engl. J. Med.,* 328:106–113.

Dulleman et al., (1995) Treatment of Crohn's disease with anti–tumor necrosis factor chimeric monoclonal antibody (cA2). *J. Gastroenterology,* 109:129–135.

Eldridge et al., (1992) Biodegradable poly(DL–lactide–co–glycolide) microspheres. *Res. Immunol.,* 143:557–563.

Eldridge et al., (1991) Biodegradable and biocompatible poly(DL–lactide–co–glycolide) microspheres . . . *Infect. Immun.,* 59:2978–2986.

Eldridge et al., (1989) Biodegradable microspheres: vaccine delivery system for oral immunization. *Curr. Top. Microbiol. Immunol.,* 146:59–66.

Ezzeddine et al., (1991) Selective killing of glioma cells in culture and in vivo by retrovirus transfer of the herpes simplex . . . *New. Biol.,* 3:608–614.

Goebel et al., (1995) Adenovirus mediated gene therapy for head and neck squamous cell carcinomas. *Ann. Otol. Rhinol. Laryngo.*

Gref et al., (1994) Biodegradable long–circulating polymeric nanospheres. *Science,* 263:1600–1603.

Hansen et al., (1989) Re–examination and further development of a precise and rapid dye method for measuring cell growth/cell kill. *J. Immun. Meth.,* 119:203–210.

Humpheries et al., (1987) Identification of two distinct regions of the Type III connecting segment of human plasma fibronection . . . *J. Biol. Chem.,* 262:6886–6892.

Hung et al., (1988) Adenovirus as the carrier for immunogen genes. *Tech. Adv. Vaccine Dev.,* pp. 267–277.

Isaacs et al., (1992) Cytokine messenger RNA profiles in inflammatory bowel disease mucosa detected by polymerase chain . . . *Gastroenterology,* 103:1587–95.

Jhon and Andrade (1973) Water and hydrogels. [Review] *J. Biomed. Mater. Res.,* 7:509–522.

Judy et al., (1995) Effectiveness of controlled release of a cyclophosphamide derivative with polymers against rat gliomas. *J. Neurosurg.,* 82:481–486.

Kaiser and McGee (1975) Aminoclygoside therapy of gram–negative bacillary meningitis *N. Eng. J. Med.,* 293:1215–1220.

Kuhn et al. (1993) Interleukin–10–deficient mice develop chronic enterocolitis *Cell,* 75:263–274.

Kunkel et al. (1991) Interleukin–8 (IL–8): the major neutrophil chemotactic factor in the lung. *Exper Lung Res.,* 17:17–23.

Langer and Folkman (1980) Sustained release of macromolecules from polymers. in *Midland Macromolecular Monograph,* ed. Kostelnik, RJ, Gordon and Breach, New York, pp. 175–195.

Langer et al., (1980) Polymers for the sustained release of macro–molecules . . . in *Controlled Release of Bioactive Materials,* ed. Baker, R Academic Press, New York, pp. 83–98.

Mansour et al., (1985) An adenovirus vector siesta used to express polymer virus tumor antigens. *Proc. Natl. Acad. Sci. USA,* 92:1359–1363.

Maron et al., (1995) Ganiclovir mediated regression of rat brain tumors expressing the herpes simplex virus thymidine kinase . . . *J. Neu–Onc.,* 24:259–265.

Mason et al., (1981) Hydrolytic degradation of poly(DL–(lactide). *Polym. Sci. Techniol.,* 14:279–291.

McCoy et al., (1995) Expression of human interleukin–1 receptor antagonist in mouse lungs using a recombinant adenovirus . . . *Gene Ther.,* 2:437–442 (1995).

McCoy et al., (1995) Pulmonary inflammation induced by incomplete or inactivated particles. *Hum. Gene Ther.,* 6:1553–1560.

Miller et al., (1977) Degradation rates of oral resorbable implants (polylactates and polyglycolates): rate modification . . . *J. Biomed. Mater. Res.,* 11:711–719.

Mombaerts et al., (1993) Spontaneous development of inflammatory bowel disease in T cell receptor mutant mice. *Cell,* 75:274–282.

Moolten and Wells (1990) Curability of tumors bearing herpes thymidine kinase genes transferred by retroviral vectors. *J. Natl. Cancer Inst.,* 82:297–300.

Mulligan (1993) The basic science of gene therapy. *Science,* 260:926–932.

Okada et al., (1991) Sustained pharmacological activities in rats following single and repeated administration . . . *Pharm. Res.,* 8:584–587.

Oldfield et al., (1993) Gene therapy for brain tumors using intra–tumoral transduction with the thymidine kinase gene . . . *Hum. Gene Ther.,* 4:39–69.

Pekarek et al., (1994) Double–walled polymer microspheres for controlled drug release. *Nature,* 367:258–260.

Peppercorn, (1992) in *Inflammatory bowel disease.* eds. MacDermott, RP, Stenson, WF, New York, Elsevier, pp. 555–577.

Perez–Cruet et al., (1994) Adenovirus–mediated gene therapy of experimental gliomas. *J. Neurosci. Res.,* 39:506–511.

Pitt, (1990) The controlled parenteral delivery of polypeptides and proteins. *Int. J. Pharm.,* 59:173–196.

Ram et al., (1994) Intrathecal gene therapy for malignant leptomeningeal nepolasia *Cancer Research,* 54(8):2141–5.

Ram et al., (1993) In situ retroviral–mediated gene transfer for the treatment of brain tumors in rats. *Cancer Research,* 53:83–88.

Ram et al., (1992) Retroviral–mediated thymidine kinase gene transfer for the treatment of malignant brain tumors. *Hum. Gene. Ther.,* 3:615 (Abstract).

Redding et al., (1984) Long–acting delivery systems for peptides: inhibition of rat prostate tumors by controlled release . . . *Proc. Natl. Acad. Sci., USA,* 81:5845–5848.

Ross et al., (1995) Assessment of ganciclovir toxicity to experimental intracranial gliomas following recombinant . . . *Clin. Cancer Res.,* 1:651–657.

Sabel et al., (1990) Extended levodopa release from a subcutaneously implanted polymer matrix in rats. *Ann. Neurol.,* 28:714–717.

Sadlack et al., (1993) Ulcerative colitis–like disease in mice with a disrupted interleukin–2 gene *Cell,* 75:253–261.

Sanders et al., (1986) Prolonged controlled–release of nafarelin, a lutenizing hormone–releasing hormone analogue . . . *J. Pharm. Sci.,* 75:356–360.

Shewach et al., (1994) Enhanced cytotoxicity of antiviral drugs mediated by adenovirus directed transfer of the herpes simplex . . . *Cancer Gene Ther.,* 1:107–112.

Short et al., (1990) Gene delivery to glioma cells in rat brain by grafting of a retrovirus packaging cell line. *J. Neurosci. Res.,* 27:427–439.

Smythe et al., (1995) Treatment of experimental human mesothelioma using adenovirus transfer of the herpes simplex . . . *Ann. Surg.,* 222:78–86.

Smythe et al., (1994) Use of recombinant adenovirus to transfer the herpes simplex virus thymidine kinase . . . *Cancer Research,* 54:2055–2059.

Takamiya et al., (1993) An experimental model of retrovirus gene therapy for malignant brain tumors. *J. Neurosurg.,* 79:104–11.

Tice and Cowsar, (1984) Biodegradable controlled release parenteral systems. *Pharmacol. Technol.,* 8:26–31.

Visscher et al., (1987) Tissue response to biodegradable injectable microcapsules. *J. Biomater. Appl.,* 2:118–131.

Alki et al., (1993) Transfer of a foreign gene into the brain using adenovirus vectors. *Nat. Genet.,* 3:224–228.

Altman and Dixon (1989) Immunomodifiers in vaccines. *Comp. Med.,* 33:301–343.

Walter et al., (1994) Interstitial taxol delivered from a biodegradable polymer implant against experimental malignant . . . *Cancer Research,* 54:2207–2212.

Wei et al., (1994) Experimental tumor therapy in mice using the cyclophosphamide–activating cytochrome P450 2B1 gene. *Hum. Gene. Ther.,* 5:969–978.

Yan et al., (1994) Characterization and morphological analysis of protein–loaded poly(lactide–co–glycolide) microparticles . . . *Controlled Release,* 32:231–241.

Yang et al., (1993) Ulcerative colitis: a genetically heterogeneous disorder defined by genetic (HLA Class II) . . . *Clin. Invest.,* 92:1080–1084.

Zentner et al., (1979) Progestin permeation through polymer membranes IV: mechanism of steroid permeation . . . *J. Pharm. Sci.,* 68:970–975.

The following is additional background material provided by the inventor.

Hilfinger et al., (1995) Stability and formulation of recombinant adenoviruses for oral delivery. *AAPS Abstract,* Nov. 1995.

Cohen et al., (1994) Novel approaches to controlled–release antigen delivery. *Int'l Journal of Technology Assessment in Health Care,* 10:1:121–130.

Niwa et al., (1994) In vitro drug release behavior of D,L–lactide/glycolide copolymer (PLGA) nanospheres . . . *J. of Pharmaceutical Sciences,* 83:5, pp. 727–732.

Calis et al., (1995) Adsorption of salmon calcitonin to PLGA microspheres. *Pharmaceutical Research,* 12:7, pp. 1072–1076.

Davidson et al., (1993) A model system for in vivo gene transfer into the central nervous system using an adenoviral vector. *Nature Genetics,* 3:219–223.

Haddada et al., in *Gene Therapy using Adenovirus Vectors.* selected pages only.

Mullen (1994) Metabolic suicide genes in gene therapy. *Pharmac. Ther.,* 63:199–207.

Freeman et al., (1996) In situ use of suicide genes for cancer therapy. *Seminars in Oncology,* 23:1:31–45.

MICROSPHERE ENCAPSULATION OF GENE TRANSFER VECTORS

GRANT REFERENCE

The research carried out in connection with this invention was supported in part by a grants from the National Institutes of Health R43 CA 67357 and R43 DK 48111. The Government has certain rights in the inventions.

TECHNICAL FIELD

The present invention relates to in vivo delivery of functional gene vectors; and more particularly, the polymeric microencapsulation of functioning gene vectors for use in gene therapy paradigms.

BACKGROUND OF THE INVENTION

The use of recombinant adenoviral vectors for delivery of genes or combinations of genes to tumor cells has been widely investigated. (Shewach et al., 1994, Davidson, 1993, Ross et at., 1995, Boviatsis et al., 1994, Barba et al., 1994, Wei et al., 1994, Mansour et al., 1985, Smythe et al., 1995, Goebel et al., 1995, Perez-Cruet et al., 1994, Chen et al., 1994, and flung et al., 1988). Recombinant adenoviruses are easily engineered to express the gene or genes desired for direct cell killing, for induction of host immune responsiveness to tumor cells, or both, and do not require mitotic activity for gene transfer expression (Davidson et al., 1993, Davidson et al., 1994, and Akli et al., 1993). Further, recombinant adenoviruses can be amplified to high titers and are amenable to formulation (Mulligan, 1993).

The ability to purify recombinant adenovirus to high titers is critical given the inefficiency of gene transfer to elements such as gliomas with a vector system. In vitro, efficacy is not noted with multiplicities of infection (MOI) below 100 infectious units per cell (Shewach et al., 1994, Chen et al., 1994). It is suboptimal below 250–500. The need for high titers, coupled to the fact that only one to five percent of virions in purified viral preps are infectious, requires high particle titers in the dosing inoculum. The resulting inflammatory response in the dosing inoculum limits the duration of gene transfer and subsequent redosing regimens (McCoy et al., 1995, McCoy et al., 1995, Barr et al., 1995, and Brynes et al., 1995).

Another problem often encountered in gene therapy regimens has to do with the host immune response following gene vector delivery. The host immune response following adenovirus delivery is robust in all tissues including brain (references). In tumor bearing hosts the response may be beneficial for therapy but detrimental to subsequent vector delivery. The T-cell response to virally infected cells may enhance killing of tumor cells (ref), but B-cell activation may result in the production of a neutralizing antibody response which limits re-infection (ref). Redosing must therefore be accomplished following an initial infection with lower titers (often not efficacious) or with virus formulated to reduce its antigenicity.

Two aims to improve the effectiveness of adenoviral mediated gene transfer for glioma therapy are to increase the efficiency of gene transfer and reduce the need for frequent re-dosing regimens. The latter can be accomplished by the sustained release of low dose adenovirus from biodegradable microspheres into the tumor mass.

Biodegradable microspheres have been successfully used to deliver drugs at a controlled rate to specific tissues, such as brain (Cohen et al., 1991, Gref et al., 1994, Okada et al., 1991, Pekarek et al, 1994, Sanders et al., 1986, Sabel et al., 1990, Judy et al., 1995, Brem et al, 1994, and Walter et al., 1994). The long term goal for the encapsulation of viral vectors for gene therapy for such diseases as tumors of the supportive glia of the brain is to provide sustained local release. As such, formulations must contain concentrated viable virus in acceptable volumes for delivery and the tissue reaction to the polymer must be minimal.

Pharmaceutical research has led to the identification of many reagents compatible with controlled delivery of drugs enterically and systemically. These reagents include hydrogels, self-diffusion and self-regulated systems, microparticles, biodegradable polymers and porous membranes (Pitt, 1990, Eldridge et al., 1991, and Eldridge, 1989). Hydrogel systems were first used for the delivery of insulin in diabetic rat models (Davis, 1972) and provide an aqueous microenvironment for the diffusional migration of macromolecular compounds. These gels limit the migration of macromolecules with a release dependent upon the polymer content of the gel and the molecular weight of the encapsulated substrate (Jhon and Andrade, 1973. Zentner et al., 1979). Self-diffusion systems allow for sustained release that it is dependent upon hydration (Sabel, 1990, Langer and Folkman, 1976, Langer and Folkman, 1978, and Langer et al., 1980), while self-regulated systems allow for controlled release by an effector molecule, (Brownlee and Cerami, 1979, Brownlee and Cerami, 1983).

Poly(lactide-co-glycolide) (PLG) copolymers have been well-characterized an offer many advantages for the sustained release of macromolecular preparations. First, PLG has well established biocompatibility and has been shown to be safe in in vivo settings (Redding et al., 1984). Degradation of PLGA in vivo occurs by acid or base catalyzed hydrolysis (Mason et al., 1981) and results in production of lactic and glycolic acids with minimal inflammatory responses (Visscher et al., 987, Tice and Cowsar, 1984). Importantly, hydrolysis rates can be adjusted by modifying the monomer ratios of the glycolic and lactic acid components (Miller et al., 1977).

Several prior art patents relate to the microencapsulation of biologicals. For example, U.S. Pat. No. 4,948,586 to Bohm et al., issued Aug. 14, 1990, discloses a microencapsulated insecticidal pathogen for application to vegetation. The insecticidal viral, bacterial, or fungal pathogen is encapsulated in a polymeric encapsulating agent.

U.S. Pat. No. 5,463,092 to Hostetler et al., issued Oct. 31, 1995, discloses lipid containing prodrugs for treating viral infections. The compounds comprise phosphonoacids having anti-viral activity which are linked to one of a selective group of lipids. A liposome is formed, at least in part, from the compositions disclosed.

U.S. Pat. No. 5,160.745 to DeLuca et al., issued Nov. 3,1992, discloses a microencapsulated biologically active macromolecular agent. The microencapsulant is a biodegradable vinyl derivative.

Referring specifically to glioblastoma, the development of alternative forms of treatment for glioblastoma, such as gene therapy, is warranted and the success of which is becoming more predictable (Moolten and Wells, 1990, Ezzeddine et al., 1991, Culver et al., 1992, Oldfield et al., 1993, Ram et al., 1993, Ram et al., 1992, Short et al., 1990, and Takamiya et al., 1993). The first clinical trials using gene therapy for the treatment of glioblastoma multiform used in situ implantation of murine retroviral producer cells. The gene transferred expressed Herpes simplex type I (HSV-1) thyrnfidine kinase (tk). This herpes gene product is not toxic but has specificity for the antiviral 2'-deoxyguanosine analog prodrug, ganciclovir. Once phosphorylated, this drug is highly toxic to mitotically active cells (Shewach et al., 1994). Because the murine based retroviruses infect only dividing cells (Moolten and Wells, 1990, Ezzeddine et al., 1991, Culver et al., 1992, and Ram et al., 1993) and in humans with glioblastoma multiform, only a small percentage of tumor cells are dividing, re-implantation of murine cells and additional rounds of high dose ganciclovir therapy are required. Immune responses to xenografts and systemic toxicity to ganciclovir are limitations of this approach.

Inflammatory bowel disease (IBD) is a second disease for which gene transfer studies have been initiated using recombinant viral vectors as a first step towards the development of an alternative therapy for the disease. IBD is estimated to affect 600,000 Americans with 40,000 new cases per year. Disabling symptoms of this disease usually begin in adolescence or early adulthood (Peppercorn Mass. 1992). Currently employed therapies directed at limiting chronic inflammation in IBD include drugs such as corticosteroids, 5-aminosalicylate (5-ASA) and immunosuppressives (e.g. irniran and 6-mercaptopurine) that have wide ranging affects on the immune system and serious side effect profiles (Peppercorn Mass. 1992).

Current understanding of the development and perpetuation of chronic intestinal inflammation in IBD suggests that there is a balance between pro-inflammatory and anti inflammatory factors. There is significant redundancy in the system so that multiple factors have overlapping roles; clearly it is the combined interaction of multiple factors that results in intestinal inflammation. Interleukin 1 (IL-1) is fundamental to many inflammatory processes including IBD (Blumberg et al., 1995, Dinarello et al., 1993, Isaacs et al, 1992). Studies suggest that it is consistently up-regulated in inflamed tissue in IBD and in many animal models of IBD (Kunkel et al., 1991. Isaacs et al, 1992). Studies of inflamed tissue from IBD patients suggest that there is an imbalance between the production of the proinflammatory IL-1 and its naturally occurring antagonist interleukcin 1 receptor antagonist protein (IL-1ra) favoring the production of IL-1 (Isaacs et al, 1992). An overall goal in the treatment of IBD would thus be to increase local expression on IL-1ra in an attempt to counterbalance the proinflammatory effects of IL-1.

An increased understanding of cytokine networks and the mechanisms of paracrine interactions between epithelial cells, mesenchymal cells, neurons and inflammatory cells in the intestinal tract has led to the development of several candidate targets for therapy of IBD. In addition to IL-1ra, anti-TNF-α monoclonal antibody and interleukin 10 (IL-10) represent cytokine-related putative therapeutic agents targets that are currently in human trial (Dullemen et al, 1995.). Delivery of these agents to the sites of active inflammation has been problematic. Systemic administration is poorly tolerated for chronic diseases such as IBD and it is difficult to deliver adequate local concentrations of the agent to perform paracrine and autocrine type functions. Since most of these putative therapeutic agents are proteins oral delivery remains difficult.

Numerous animal models for IBD, such as the rabbit model of formalin-immune complex colitis (Comanelli et al., 1990.), IL-10 knockout mice (IL-10T mice) (Kuhn, et al., 1993), IL-2 deficient mice (Sadlack et al., 1993), and the T-cell receptor knockout mouse (Mombaerts et al., 1993), enable the determination of whether cytokine-mediated therapy can inhibit the onset and progression of disease. Treatment of rabbits having formalin-immune complex colitus with bolus i.v. injections of IL-1ra protein significantly reduced the inflammatory response associated with the experimental colitus (Cominelli et al., 1990). Further, in IL-10T mice, bolus injections of IL-10 (10 ug) 30 minutes prior to challenge with lipopolysaccharide (LPS), prevented endotoxic shock. More importantly, treatment of IL-10T mice by i.v. injection of an adenovirus containing the human IL-10 cDNA protected 67% of animals (n=6) from LPS challenge 9 days after infection. Those animals that survived the challenge were found to contain high plasma levels of IL-10 (>200 picograms/ml) and all of these animals withstood a second challenge 20 days after adenoviral infection. Animals (n=7) that were infected with Ad.RSVlacZ at similar doses did not survive LPS challenge. It can be concluded from these studies that adenoviral-mediated expression of pharmacologically relevant levels of gene products can alter the natural history of diseases such as IBD.

It is desirable to provide a delivery system for functional gene vectors and specifically for recombinant adenovirus. It is further desirable to derive a biodegradable microsphere used for delivery system deliver functional genes. More specifically, it would be desirable to provide a means for delivering adenoviral vectors for gene therapy such as for the treatment of intracerebral glioma, inflammatory bowel disease, and other diseases.

SUMMARY OF THE INVENTION AND ADVANTAGES

In accordance with the present invention, there is provided a controlled release delivery system which includes a functional gene vector and a biodegradable polymer microsphere encapsulating the vector. The present invention further provides a method of making a controlled release delivery system by encapsulating a functional gene vector and a biologically degradable polymeric microsphere.

BRIEF DESCRIPTION OF THE DRAWINGS

The file of this patent contains at least one drawing executed in color. Copies of this patent with color drawings will be provided by the Patent and Trademark Office upon request and payment of the necessary fee.

Other advantages of the present invention will be readily appreciated as the same becomes better understood by reference to the following detailed description when considered in connection with the accompanying drawings wherein.

DETAILED DESCRIPTION OF THE INVENTION

Figure 1A:
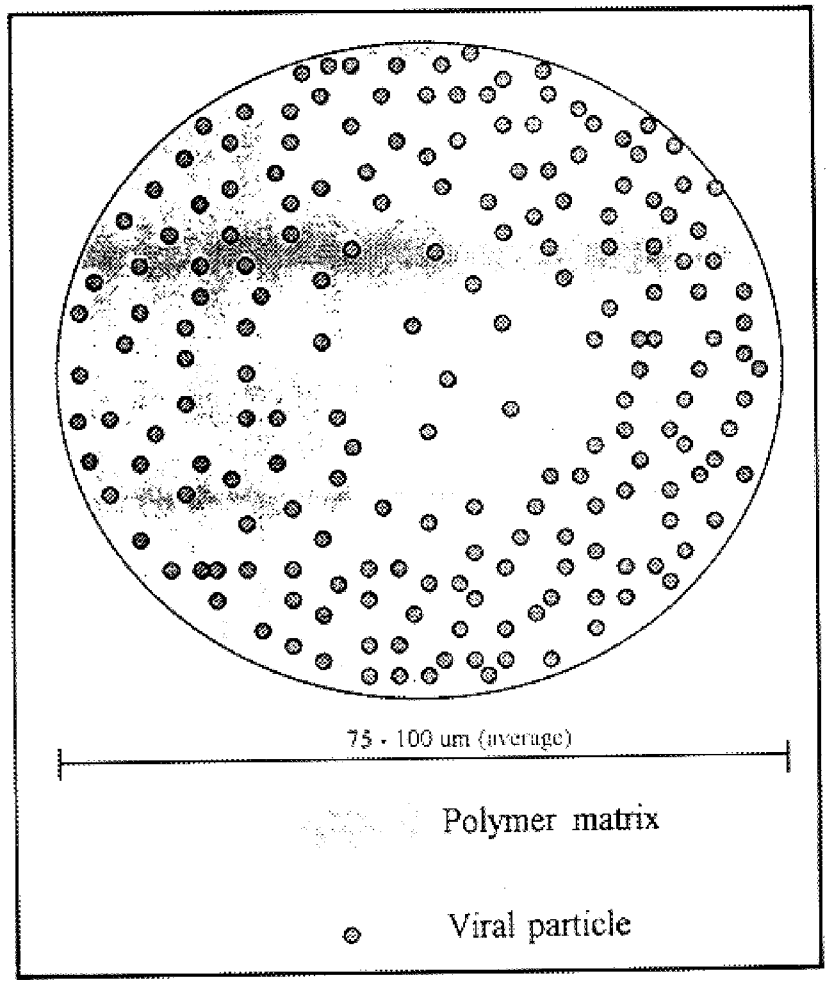
FIG. 1A shows theoretical microsphere formation.

In general, the present invention provides a controlled release delivery system including a functional gene vector and a biodegradable polymer microsphere encapsulating the vector.

More specifically, the term "controlled release delivery system" means a drug delivery system providing controlled release either by time or by location or both. That is, the system is designed to allow release of the contents thereof by either controlled rate or a controlled time, or at a desired site. For example such systems have been developed in the past for immediate release of what may be considered a loading dose and then later release for maintenance over an extended period of time. Alternatively, or in combination, a coating may be applied, that is of the type which dissolves under specific ionic or acidic conditions so as to deliver the contained vector at a desired destination. For example, the coating may be of the type for dissolving in acidic conditions for delivery to the stomach. Such coatings, in general, are well known in the art. Examples of such coatings are which are insoluble in neutral pH (i.e., in the mouth) and are soluble in acidic pH to provide specific delivery to the stomach. Examples of such coatings include the Eudragit E series of copolymers—poly[butyl methacrylate, (2-dimethyl aminoethyl) methacrylate, methyl methacrylate].

Alternatively, the coating can be enteric in nature so as to either dissolve specifically in the small or the large intestine. Examples of such enteric coatings used in the prior art are cellulose acetate phthalate, hydroxymethylpropyl cellulose, and polymethacrylates (Eudragit L and S series of copolymers).

By functional gene vector, it is meant that the present invention provides for delivery to a desired site. That is, a gene vector capable of incorporation and function within the target cell. Preferably, the present invention provides a gene vector selected from the group consisting of viruses, bacteriophage, plasmids, and purified DNA fragments.

More preferably, the present invention provides a means of delivery for recombinant adenoviruses, separately or in combination that are derived from the known adenoviral serotypes, such as serotypes 2, 5, 12, 40, and 41. Most preferably, the present invention provides a means of delivery for a recombinant adenovirus, serotype 2 or 5, which is replication-deficient. The replication-deficient adenovirus can contain the thymidine kinase (tk) gene from herpes simplex virus, type I, under control of the Rous Sarcoma Virus (RSV) promoter (Ad.RSVtk). Another virus suitable for the present invention is the replication-deficient adenovirus with the E.coli beta-galactosidase gene, lac Z, under control of the RSV promoter (Ad.RSVlacZ). A third example of a suitable recombinant adenovirus is the human interleukin 1 receptor antagonist gene under control of the RSV promoter, Ad.RSVIL-1ra. A fourth example of a suitable recombinant adenovirus contains the human IL-10 gene under control of the RSV promoter (Ad.RSVIL-10). Other recombinant adenoviruses, derived from any of the known serotypes, and potentially with different promoter systems can be used by those skilled in the art. Other gene vectors can also be used by those skilled in the art.

The biodegradable microspheres encapsulating the vector of the present invention are preferably made utilizing polymers and copolymers selected from the group including poly (lactide-co-glycolide) (PLGA), hydroxypropylmethyl cellulose phthalate, cellulose acetate phthalate, and the Ludragit R, L, and E series of polymers and copolymers.

Preferably, PLGA co-polymers are used as they have been well characterized and offer many advantages for sustained release of macromolecular preparations. As stated above, PLGA has well established biocompatability and has been shown to be safe in in vivo settings. (Redding, 1984). PLGA will degrade in vivo by acid or base catalyzed hydrolysis and results in production of lactic or glycolic acids with minimal inflammatory responses to the surrounding tissue (Mason et al., 1981, Visscher et al., 1987, Tice and Cowsar, 1984). Most importantly, hydrolysis rates can be adjusted by modifying the monomer ratios of the glycolic and lactic acid components (Miller et al., 1977). For example, lactide to glycolide ratios can range from 50:50 lactide to 100% to lactide:0% glycolide.

The microspheres of the present invention can range in size from one micron to 200 microns. Preferably, microspheres range in size between about one to one hundred fifty microns. Most preferably, the sizes range from ten to one hundred fifty microns. The smaller the microsphere diameter, the greater the surface area per unit mass. Hence, the smaller the microsphere, the faster the release rate of encapsulated drug. Thus, in vitro studies using microencapsulated norethisterone found that an increase in diameter of PLGA microspheres from 54 to 107 microns resulted in a 4 fold increase in the initial release rate of drug (Cowsar et al., 1985). Similar findings were reported for release of protein from PLGA microspheres (Yan et al., 1994). Factors most affecting the particle size of the microsphere include the initial concentration of the PLGA polymer and the method used to form the emulsion. The size of the microspheres can effect distribution, pharmacokinetics, and other factors as is well known by those skilled in the art.

The present invention can also be utilized to co-administer vectors and drugs which work in combination. For example, current protocols employ the systemic administration of ganciclovir (GCV) to tumors treated previously with AdRSVtk. Perez-Cruet et al. showed that with systemic doses of GCV above eighty milligrams per kilogram, it was possible to eradicate tumors in a rat model following even a single dose of Ad.RSVtk. However, the high toxicity of systemic GCV limits the dose which can be given in humans, (15 milligrams per kilogram), and thereby reduces efficacy. The present invention provides a means for providing a local concentration of GCV which can be increased to the level achieved by Perez-Cruet et al. thereby making treatment with virus more efficacious. The present invention further provides a means for delivering the dose intratumorally, thereby avoiding systemic toxicity. The present invention provides for encapsulation of the Ad.RSVtk virus, preferably utilizing PLG, designed for local delivery of both virus and high concentrations of GCV augmenting therapy.

By way of background, previous investigations have evaluated intrathecal administration of GCV for tk-mediated cell killing (Ram, 1994). While these studies showed little central nervous system (CNS) toxicity for this form of therapy, they also showed poor efficacy compared to treatment with systemically administered GCV. However, when utilizing the intrathecal route of administration for pharmaceutical agents, the dynamics of cerebral spinal fluid (CSF) flow must be taken into consideration. Anti-microbials administered into the CSF have been shown to attain different levels in various regions of the CNS depending on the location where the agents were introduced (Kaiser and McGee, 1975). A homogenous equilibrium of drug levels does not occur within the CSF. On the other hand, delivering agents directly to the desired location of action has been done effectively with chemotherapeutic agents (Brem et al., 1994, Judy et al., 1995, Walter et al., 1994), thus circumventing the effect of CSF regional concentration gradients. In this manner, encapsulated GCV can be delivered in accordance with the present invention directly to the tumor bed affording a high local sustained concentration of prodrug thereby improving efficacy.

The present invention further provides, in general, a method of making a controlled release delivery system by encapsulating a functional gene vector in a biologically degradable polymeric microsphere. The step of encapsulating the functional gene vector is achieved by adding the functional gene vector to a polymeric solution and first forming a water-oil emulsion and then forming a water-oil-water emulsion of microspheres encapsulating the gene vector and then separating the formed microspheres from the remaining solution.

More specifically, the encapsulation process involves the formation of double emulsions consisting of oil-water layers by methods previously disclosed (Cowsar et al., 1985). FIG. 1A shows theoretical microspheres formation. PLGA microspheres theoretically form with the aqueous layer containing the adenoviral vector surrounded by polymer.

The molecule being encapsulated, such as viral vector, is dissolved in aqueous solution. As seen in the experimental section below, the addition of certain compounds, such as bovine serum albumin (BSA), enhances the overall release and release rate of adenovirus from microspheres. For encapsulation of adenovirus, Polymer, preferably (PLGAA 50:50), Birmingham Polymers, is dissolved in methylene chloride and virus is then added. However, other solvents can be utilized as exemplified in the experimental section below. Mixing can be accomplished by vortexing or sonification, resulting in the formation of an oil/water emulsion. The oil-water emulsion is then mixed with a second aqueous solution to form a water/oil/water double emulsion. The second aqueous solution can contain a surfactant, preferably polyvinyl alcohol (PVA) at concentrations ranging from 0.1% to 5% The PVA can be of low, medium or high viscosity grace. The PVA assists in maintaining the structural integrity of the microspheres. The water/oil/water double emulsion is further diluted into 0.1% PVA in water and gently stirred. To aid in removal of the organic phase, the water/oil/water double emulsion can be extracted with isopropanol or placed under a gentle vacuum with stirring. After a stirring period of 0.5 hours to 4 hours, the wet spheres are collected by either filtration or by gentle centrifugation and are then washed.

Figure 1B:
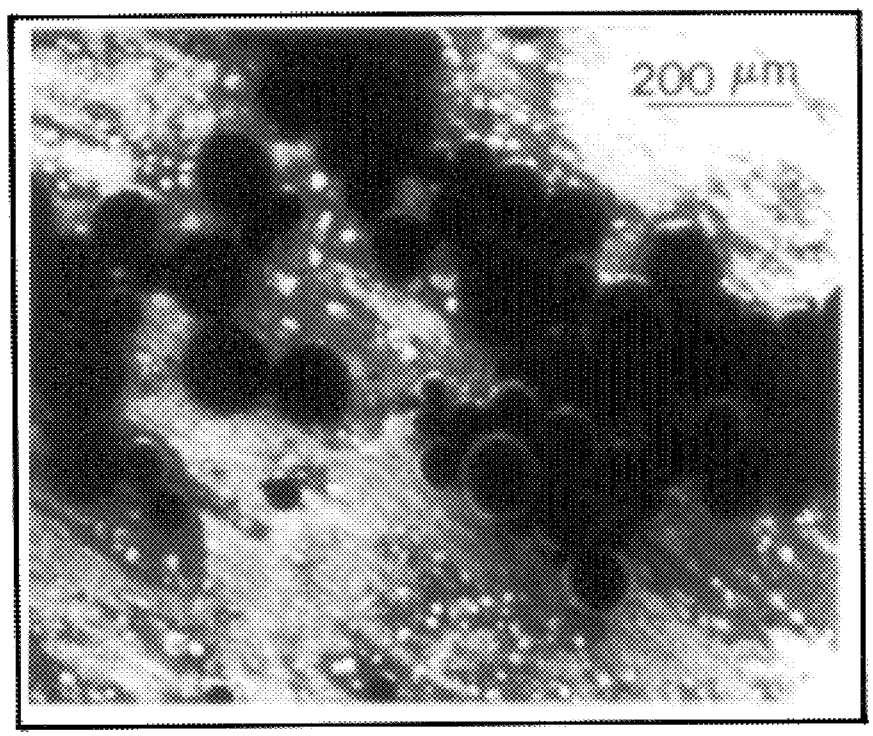
FIG. 1B shows scanning electron microscopy of actually formed microspheres.

Although filtration sieves can be used to select microspheres based on size, several the experiments were done with an unsieved preparation. Using these methods, the sizes generally range from ten to one hundred fifty micrometers, as shown in FIG. 1B. FIG. 1B is a scanning electron micrograph of microspheres formed in accordance with the present invention. The scanning electron micrograph of microspheres followed encapsulation of adenoviral vectors. Microspheres were prepared in the standard fashion as set forth above and were fixed in osmium tetroxide vapor. Microscopy was performed with a Hitachi 2460N microscope at variable pressures between seventy and one hundred Pascals using a fifteen kilovolt beam. The scale bar on the micrograph equals two hundred microns.

For treatment of glioblastoma, the present invention can be used in conjunction with currently used protocols for tumor resection and stereotactic surgery (Bernstein et al., 1993) to prevent the regrowth of the tumor. The microspheres in the present invention are amenable to passage through a narrow gauge needle (>~400 microns) and can be delivered to the tumor bed with such a device.

The present invention can be used in the treatment of many other types of tumors in which resection of the tumor is a typical method of treatment. Further, it could be used in combination with or in place of tumor resection

EXPERIMENTAL SECTION

The following experiments demonstrate methods of preparation of the present invention. The experiments further demonstrate release capabilities of the microspheres made in accordance with the present invention. This section also demonstrates various species of the present invention for use in areas such as anti-tumor therapy, therapy for inflammatory bowel disease, as well as being applicable to other areas of use.

Experiment 1
Release of Recombinant Adenovirus from PLGA Microspheres:

Encapsulation yields of 13% to 18% of the starting viral stock were typical, based on encapsulation and release data using [$^{35}$S]-metabolically radiolabeled adenovirus pursuant to the method of formation described above. To determine release rates, radiolabeled virus in microspheres were incubated in PBS in a humidified $CO_2$ incubator for indicated periods of time, and aliquots were removed and measured for the presence of label. For calculation of the total amount of radiolabled virus encapsulated, spheres were dissolved in methylene chloride and counted.

Figure 2:
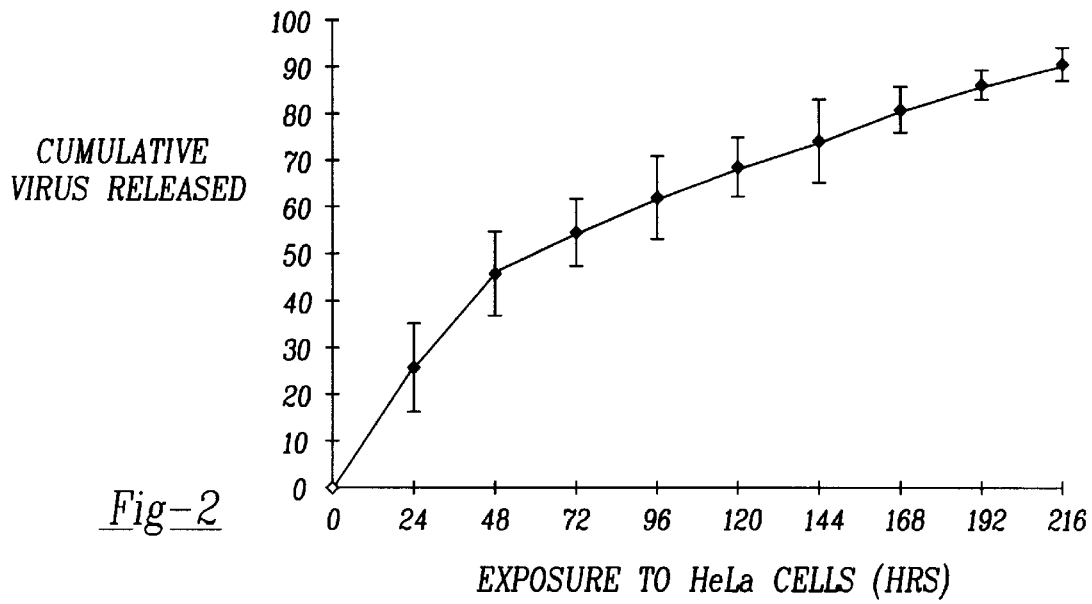
FIG. 2 is a graph showing the release of radiolabeled encapsulated virus, the adenovirus being metabolically labeled with $^{35}$S-Met, purified and encapsulated in PLGA.
Figure 3:
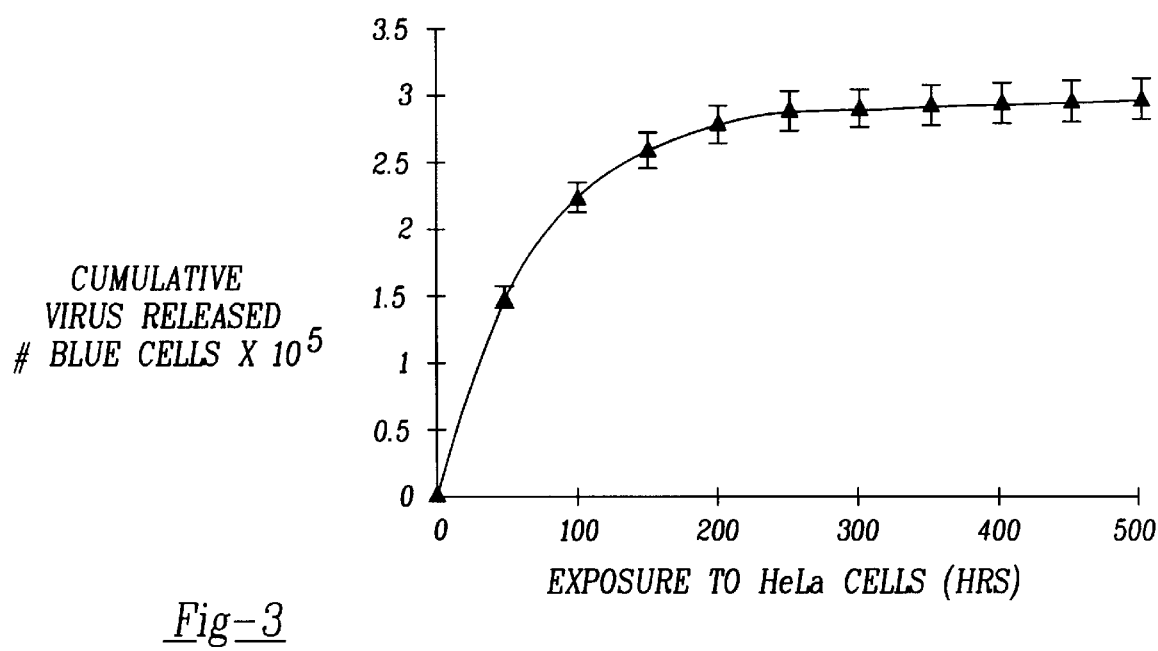
FIG. 3 is a graph showing the release of viable virus from microspheres wherein AdRSVlacZ was encapsulated and exposed to HeLa cells for the periods of time indicated on the graph, the cells were rinsed to remove microsphere, fixed in 0.5% gluteraldehyde, washed, and stained in X-gal for assessment of β-galactasidase activity.

As seen in FIG. 2, 60% of the encapsulated virus was released over the first three days of incubation. An additional 30% was released over the next 12 days. These data suggest that nearly all of the encapsulated virus can be released from PLGA microspheres The viability of vectors after release from the polymer was tested by gene transfer assays. The virus used in these studies contains the *E. coli* β-galactosidase gene, lacZ, under control of the Rous Sarcoma Virus (RSV) promotor (AdRSVlacZ). Aliquots of conditioned medium from encapsulated AdRSVlacZ were incubated with HeLa cells and the cells were incubated for an additional 24 hours. The cells were fixed, stained, and lacZ gene transfer evaluated by direct counting of transduced cells (Shewach et al., 1994). Alternatively, encapsulated AdRSVlacZ was placed in transwell inserts (Costar) over cells for fixed time periods, transwells removed and the media was replaced. Cells were stained for β-galactosidase activity 24 hours later. Using both techniques, viable virus was released from the microspheres. Gene transfer peaked within three days and was continually detected for 15 days (see FIG. 3). Estimations of yields of viable virus released ranged from 0.1 to 1.0% of the final amount of virus encapsulated. Formulation with higher concentrations of bovine serum albumin (BSA) increased the amount of virus capable of mediating gene transfer 25-fold (see Experimental Section III), apparently by stabilizing the virus during encapsulation. Alternatives to BSA will be required for microencapsulation for in vivo use, and are the basis for ongoing collaborative studies.

Figure 4:
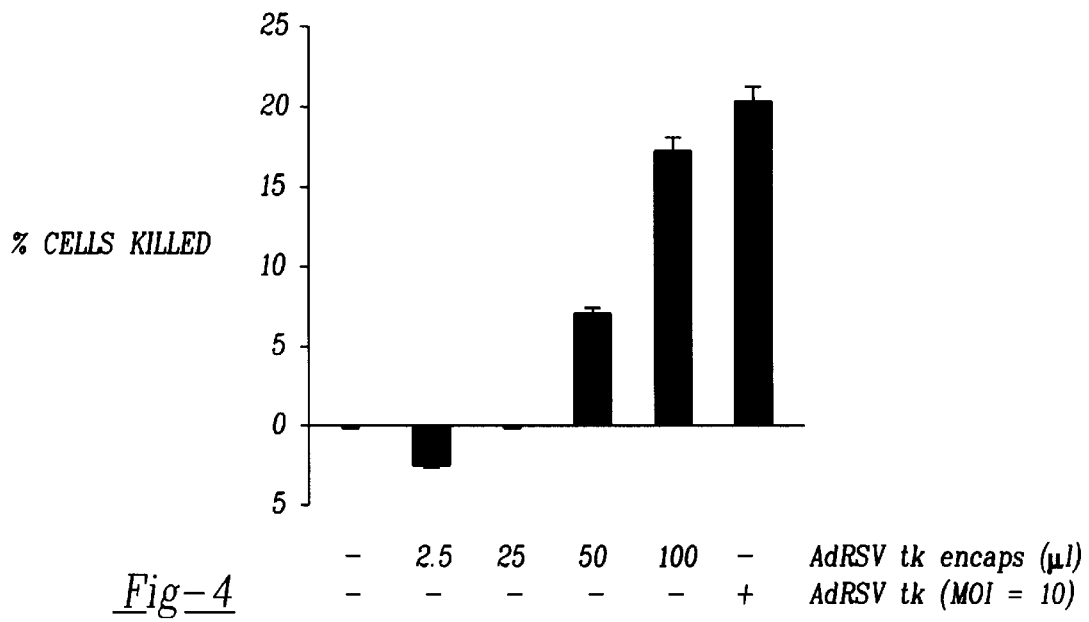
FIG. 4 is a bar graph showing the cytotoxic effect of encapsulated AdRSVtk wherein increasing amounts of diluted microspheres containing AdRSVtk were exposed to 9L gliosarcoma cells for ten days, Ganciclovir was added (1.0 μm) and the cells were trypsinized and re-seeded. The number of viable remaining cells were quantitated five days later using MTT. The negative control received no virus whereas the positive control received unencapsulated AdRS-Vtk ($10^7$ infectious units)

Evaluation of in vitro efficacy:

Microencapsulated recombinant adenovirus containing the HSV tk gene (AdRSVtk) was tested for cytotoxic effects on 9L gliosarcoma cells. Increasing doses of AdRSVtk microspheres were exposed to 9L cells in culture for 10 days, after which the cells were washed, trypsinized and re-plated. Ganciclovir (1.0 μM) was added and cell survival was assessed five days later. A dose dependent increase in cytotoxicity was observed (see FIG. 4) with a 16% cell kill noted at the highest dose. This concentration of microspheres resulted in the same level of cytotoxicity as $10^6$ unencapsulated infectious units of AdRSVtk. This encapsulated dose and volume are achievable in vivo. This level of gene transfer reduced tumor burden. Improvements in encapsulation yields, will substantially increase in vivo efficacy.

Figure 5:
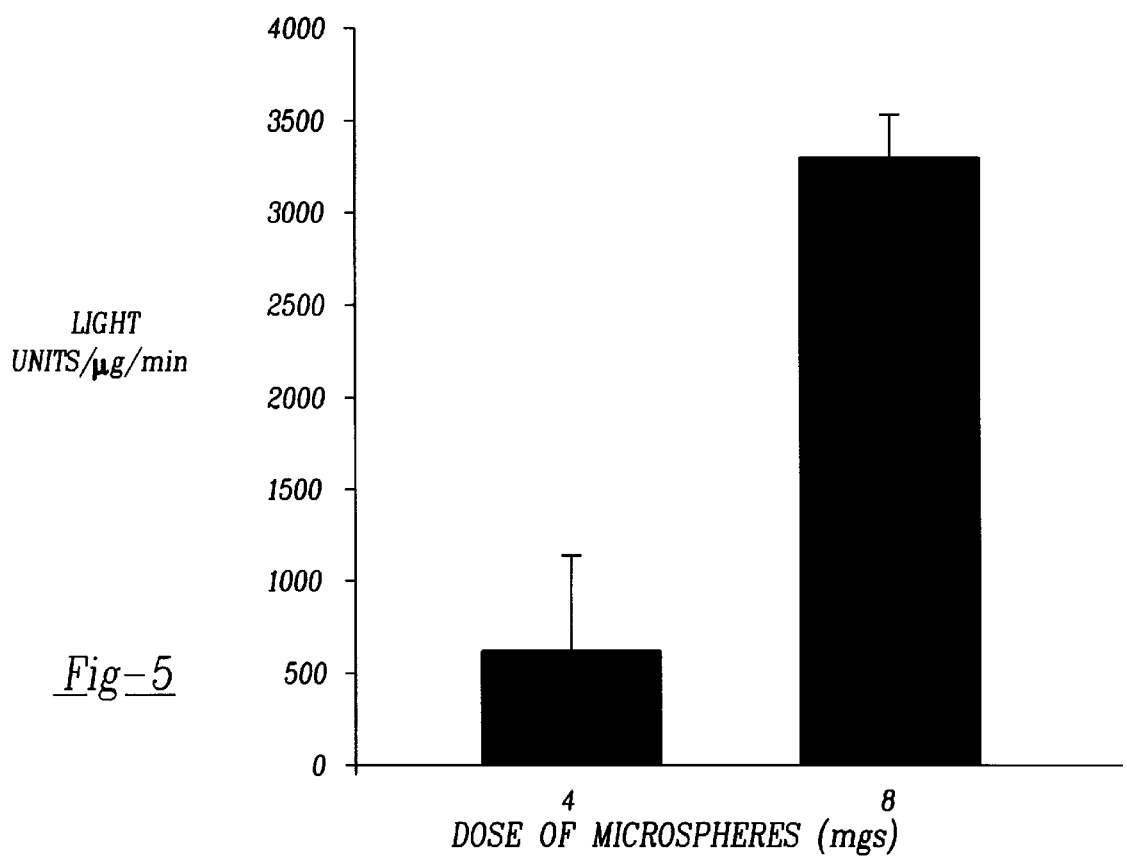
FIG. 5 is a bar graph showing the gene transfer in vivo with encapsulated adenovirus, increasing volumes of encapsulated AdRSVlacZ (estimated encapsulated infectious units was $6\times10^4$ to $1.2\times10^5$ for four and eight milligrams, respectively) were injected into the striatum of C5 FDL/6 mice. The animals were sacrificed and the brain harvested seven days post injection for lacZ activity assay using a β-galactosidase quantitation kit (Tropix, Inc.)

In vivo gene Transfer with Microencapsulated Adenovirus:

AdRSVntlacZ was encapsulated using the procedures described above, and 4 or 8 μl (1 mg/μl) of washed microspheres were suspended in PBS and inoculated into the striata of mice. Control animals received a dose of $1 \times 10^7$ infectious units of encapsulated AdRSVntlacZ. This dose is 100 to 500 fold higher than the amount of virus delivered in the microspheres. Animals were sacrificed seven days later and β-galactosidase measured (Tropix, Inc.). A dose dependent increase in β-galactosidase activity was noted as shown in FIG. 5.

Applications and Limitations Based on Above Data:

Adenoviral mediated gene transfer for treatment of glioblastoma is not yet efficacious due to the high multiplicity of infection needed for efficient gene transfer and the need for re-dosing. Also, the toxicity of phosphorylated GCV is limited to the proportion of cells undergoing mitosis and, as such, further dosing is required for infection of cells entering the cell cycle. Microencapsulation of recombinant adenoviral vectors allows for prolonged exposure of the tumor mass to viable virus, thereby increasing the number of transduced cells and hence efficacy. To test this hypothesis, experiments on the microencapsulation recombinant adenovirus using PLGA were done as set forth above.

The data suggest that viable virus can be delivered from a PLGA microsphere preparation in vitro and in vivo Studies by others have shown that decreased sphere size results in improvements in encapsulation yield (Eldridge et al., 1992). However, no studies to date have been done to optimize the encapsulation of live viral vectors. Given the relatively large size of the adenovirus (approximately 100 nm) and consideration of mechanical forces upon encapsulation, gentle methods for encapsulation were used which resulted in large (>10 to 20 μm) sphere size. This size is advantageous when delivering the antigenic adenovirus. Experiments which directly compare the immune response to antigens in 1–10 vs. 10–110 μm spheres show a 20-fold reduction in immunogenicity when encapsulated in larger particles (Eldridge et al., 1991.). Others have also shown a reduction in immune responses to antigyens of the hepatitis B virus when encapsulated in PLGA (Alitman and Dixon, 1989)

Experiment Section II
Experimental Methods:

Adenovirus: The lacZ adenovirus, Ad.RSVlacZ, was generated by homologous recombination following transfection of the plasmid shuttle vector containing lacZ and purified sub360 DNA in permissive 293 cells.

Adenoviral assay: Serial dilutions of aclenoviral solution were added to the indicator cell line 293. After an 18 hour incubation period, the cells were washed with PBS, fixed in glutaraldehyde, and stained with 1 mg/ml 5-bromo-4-chloro-3-indolyl-β-galactoside. The titer (lac formating units or lfu) of the viral solution was calculated by multiplying the average number of stained cells per microscopic field by the magnification constant (385x) and the dilution factor.

Microsphere formation: 50 μl of either viral solutions ($3 \times 10^8$ lfu) or BSA solution was added to one ml of freshly prepared PLGA solution (ranging from 10% to 30% copolymer in methylene chloride). The water/oil emulsion was formed by vortexing for 30 seconds. The water/oil/water emulsion was formed by addition of this solution to 2 ml of 1% PVA, followed by vortexing for 30 seconds. The resulting double emulsion was poured into 100 ml of 5% isopropanol in water and was stirred for 30 minutes followed by 30 minutes of additional stirring under vacuum to remove the organic solvent. Finally, the microsphere preparation was filter washed with at least 200 mls of PBS to remove unencapsulated virus, using a 0.2 μm filter.

Release Studies from PLGA Microspheres:

Encapsulated virus was added to the upper chamber of a Transwell® tissue culture insert (0.4 micron mesh, Costar). Medium from the lower chamber was sampled at the indicated times and assayed for viral activity. For encapsulated protein release, aliquots of microspheres were incubated in PBS at 37° on a rocking platform. The protein concentration of the supernatant was determined at the indicated times using the Bio-Rad Protein Assay.

Figure 6:
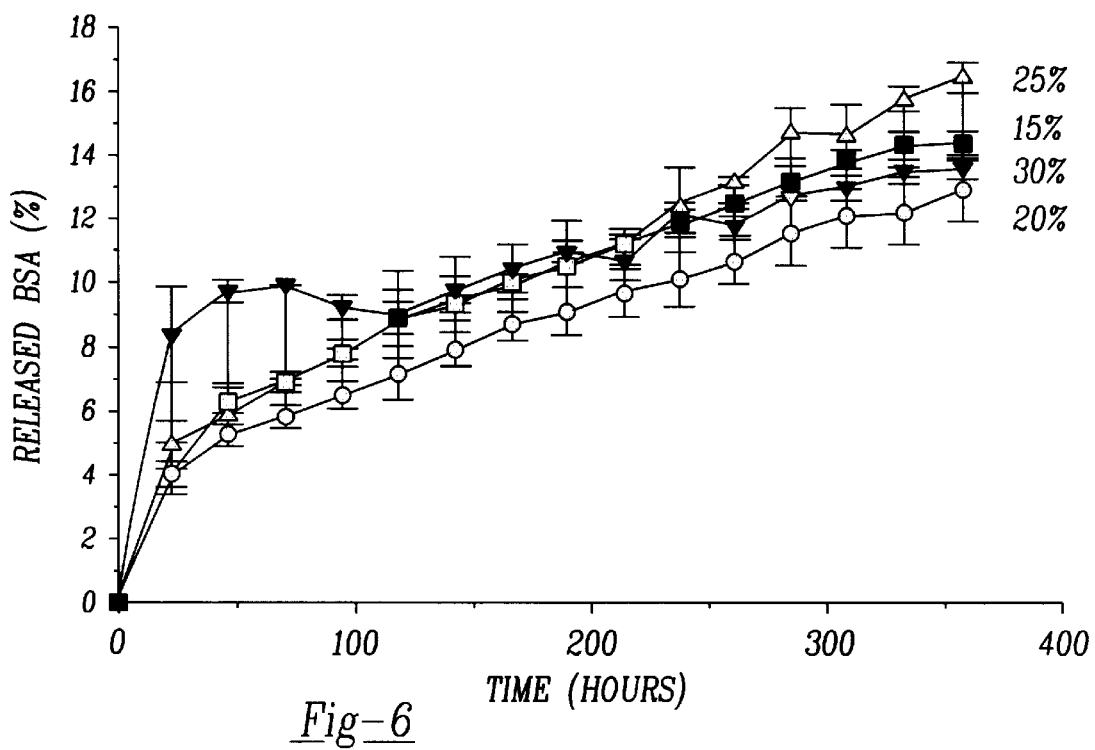
FIG. 6 is a graph showing the release of BSA from microspheres as a function of PLGA concentration.
Figure 7:
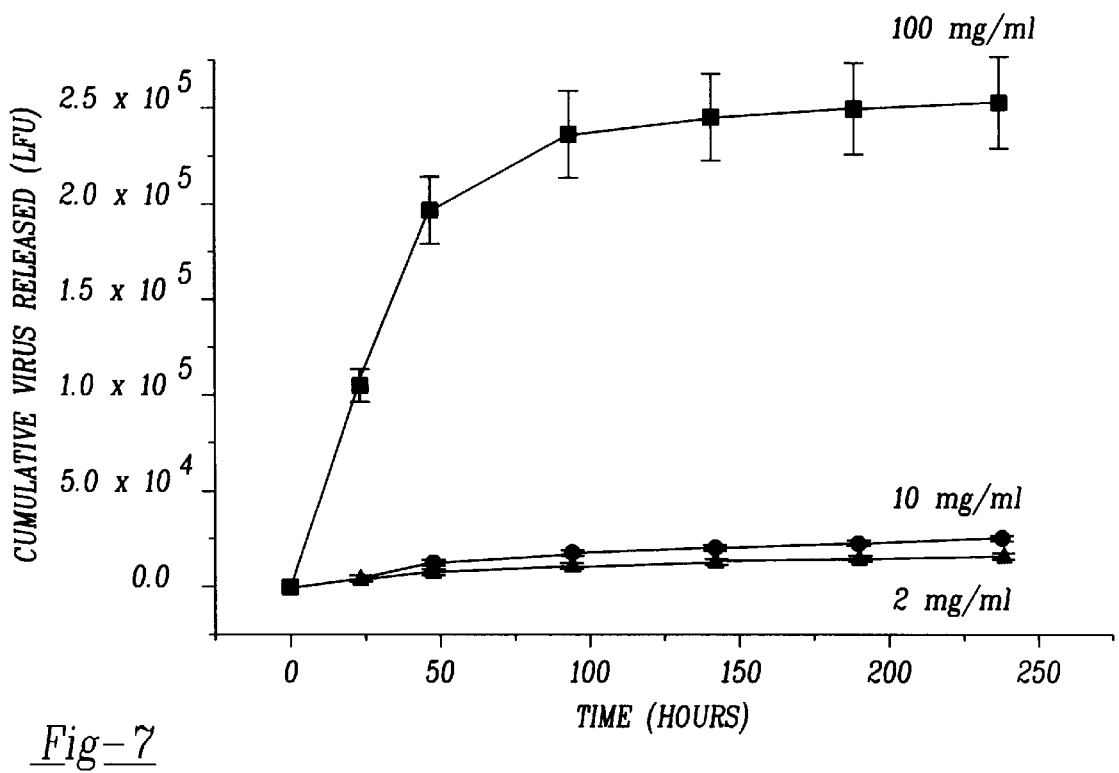
FIG. 7 is a graph showing the effect of BSA on release rates of encapsulated adenovirus microspheres over time.
Figure 8:
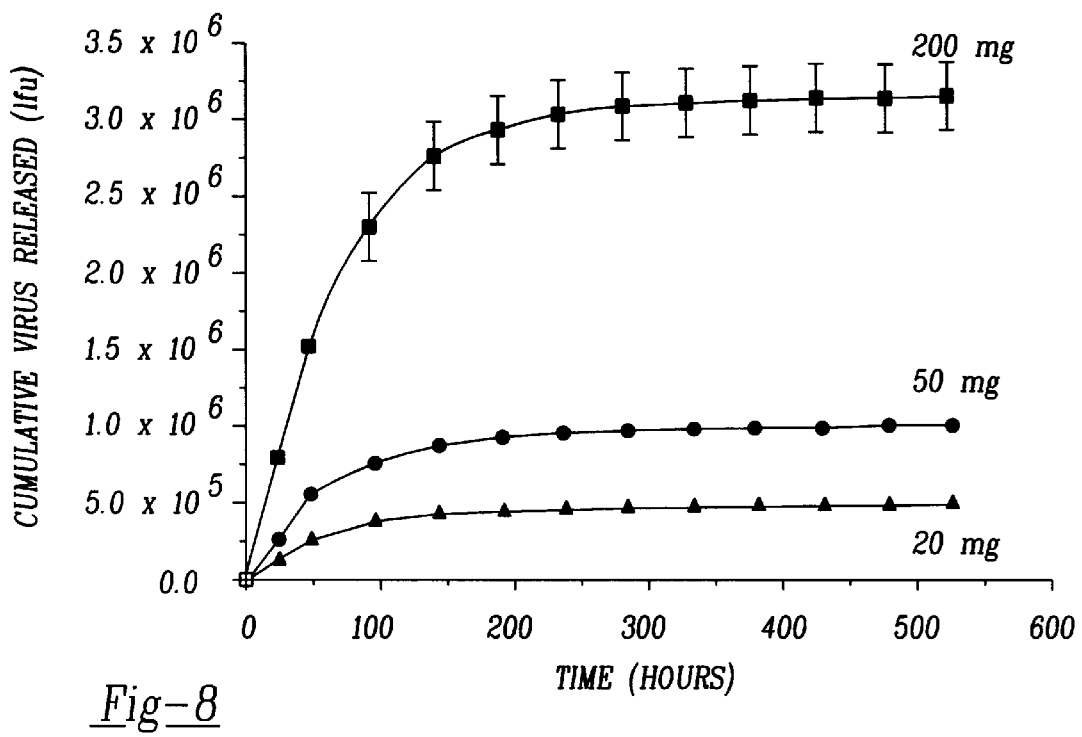
FIG. 8 is a graph showing the release of adenovirus versus time as a function of milligrams of microspheres.

Results:

The size of the microspheres formed from this procedure ranged from 1 to >100 microns. In initial experiments, the effect of a number of different parameters on the release of encapsulated BSA, including PLGA concentration PLGA composition and length of vortexing time were examined. As an example, FIG. 6 shows the effect of varying PLGA concentration during the encapsulation procedure on release of BSA from microspheres. In all cases, a biphasic release profile was seen, with an initial rapid release of ~5% to 10% of the total protein within 24 hours, followed by a slower extended release of protein over the remainder of the experiment. For viral release from microspheres, it was found that BSA acted as a stabilizer during the encapsulation procedure. As seen in FIG. 7, increasing the concentration of the BSA to 100 mg/ml or greater in the viral solution during the formation of the first emulsion resulted in a vast increase in the amount of virus released. FIG. 8 shows the increase in viral release as a function of the amount of microspheres. Routinely, the release of approximately $3 \times 10^6$ active viral particles over the course of 12 days was achieved.

Conclusions:

As seen in Table I, approximately 1% of the input virus was recovered.

TABLE 1

Initial amount of virus, unencapsulated, and the amount released from PLGA microspheres.

| stage of encapsulation | viral activity (lac forming unit) |
| --- | --- |
| starting material | $3.0 \times 10^8$ lfu |
| unencapsulated | $3.7 \times 10^7$ lfu (12.3%) |
| released | $3.0 \times 10^6$ lfu (1.0%) |

At this stage, it is unclear whether the low release amount reflects low encapsulation efficiency, viral inactivation during the encapsulation procedure, or simply low release rates from the microspheres.

Experimental Section III

Materials and Methods

Microsphere Encapsulation of Virus

1. Poly(lactic-glycolic) acid (PLGA) was dissolved in 1 ml of dichloromethane and mixed with 0.05 ml of aqueous suspension of virus. Additions to the viral encapsulation buffer can include glycerol, sucrose, and bovine serum albumin (BSA). In initial experiments to test some of the parameters of the encapsulation technique, only BSA was encapsulated.

2. The solution was vortexed for 0.5 minute to form a water-oil emulsion.

3. The water-oil emulsion was added to one ml of 1% poly (vinyl alcohol) (PVA) and vortexed for an additional 0.5 minute to form a water-oil-water emulsion.

4. The water-oil-water emulsion was added to 100 ml of 0.1% (PVA) and stirred for an additional 30 minutes.

5. A vacuum was applied to the solution to facilitate the removal of dichloromethane and stirring was continued for 2.5 hours.

6. The resulting microspheres were filtered on 0.2 $\mu$m nylon filters and washed with 500 ml PBS.

Modifications to this Method Include:

A. Increasing the initial volume of aqueous solution up to 0.1 mls in Step 1.

B. Also in Step 1, a drug, ganciclovir (GCV), can be encapsulated in place of or along with the adenovirus. This modification is directed at the treatment of tumors with a specific adenovirus, Ad.RSVtk, which contains a "suicide" gene that works in conjunction with the GCV to promote cell death. Although the incorporation of drug within PLGA polymer microspheres is not new, there is no evidence to date to show the combination of drug and biological agent (Adenovirus) delivered in such a manner has been accomplished.

C. The length of time of vortexing in Steps 2 and 3 can be varied up to two minutes without significant change to the appearance of the microspheres.

D. In Step 4, the spheres can be added to a solution of 5% isopropanol (100 to 200 mls), stirred for 30 minutes with or without vacuum, and filtered.

E. In Step 6, spheres can simply be washed extensively and collected by centrifugation (~1000×g) instead of filtered.

DATA

Methods Used to Test Encapsulation Technique:

Electron microscopy: Specimens for scanning electron microscopy were analyzed immediately after preparation with a Hitachi 2460N microscope at a variable pressure between 70 and 100 pascals using a 15 kilovolt beam. Additional spheres were examined using similar parameters following vapor fixation in osmium tetroxide.

Release of virus from PLGA microsphere: PLGA encapsulated virus was incubated in either PBS or 2% DMEM while being rocked slowly on a Labquake shaker (Barnstead/Thompson) at 37° C. 5% $CO_2$. At indicated intervals, an aliquot of supernatant was removed and assayed for viral activity. An alternative method was employed in which the microspheres were placed in the upper chambers of a six well dish fitted with transwell inserts (Costar). Transwell inserts with either 3 or 0.4 micron filters prevented the microspheres from entering the lower chamber. In transwell experiments, the medium was completely removed from the lower chamber, replaced with fresh medium, and assayed for viral activity.

BSA: BSA-encapsulated microspheres were incubated in PBS. Aliquots were removed every 24 hours and replaced with fresh buffer. The protein concentration of the aliquots was determined with a BioRad protein assay following the manufacturer's protocol.

Ad.RSVntlacZ: To measure the release of Ad.RSVntlacZ from encapsulated preparations, aliquots of medium conditioned by encapsulated Ad.RSVntlacZ were incubated with the 293 indicator cell line for 2 hours, after which time, serum and fresh DMEM were added to bring the final serum concentration to 10%. The cells were incubated an additional 16 hours, then stained with X-gal following standard laboratory procedures. The average number of blue stained cells was determined in a minimum of 20 fields, then multiplied by the magnification and dilution factors to determine lacZ forming units (LFU).

Ad.RSVtk: Cytotoxicity of Ad.RSVtk infection followed by GCV incubation was assessed with a clonal MTT. 1.5× $10^6$ 9L cells were incubated in a T-25 flask with encapsulated virus or control samples of virus for the indicated amounts of time. The cells were trypsinized and re-seeded into 6 wells of a 24 well plate. After 24 hours, 1 $\mu$M GCV was added and the incubation was continued for an additional 3 to 5 days. The cell number was determined by MTT staining (Hansen et al., 1989). All viruses were generated by Dr. Davidson for use in these studies.

Figure 9A:
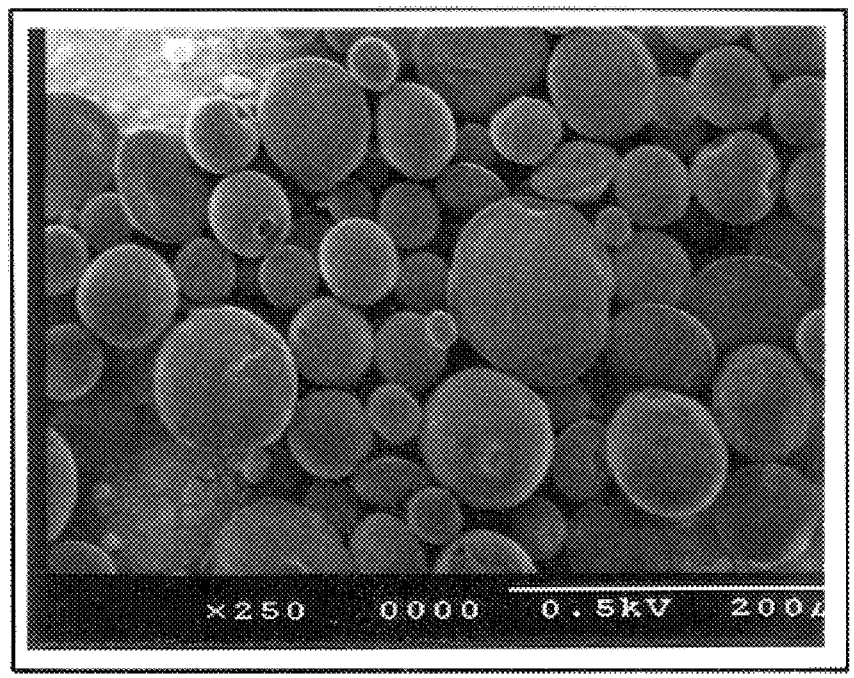
FIG. 9A is a SEM photograph of a typical preparation of Ad.RSV-microspheres magnified 250 times.
Figure 9B:
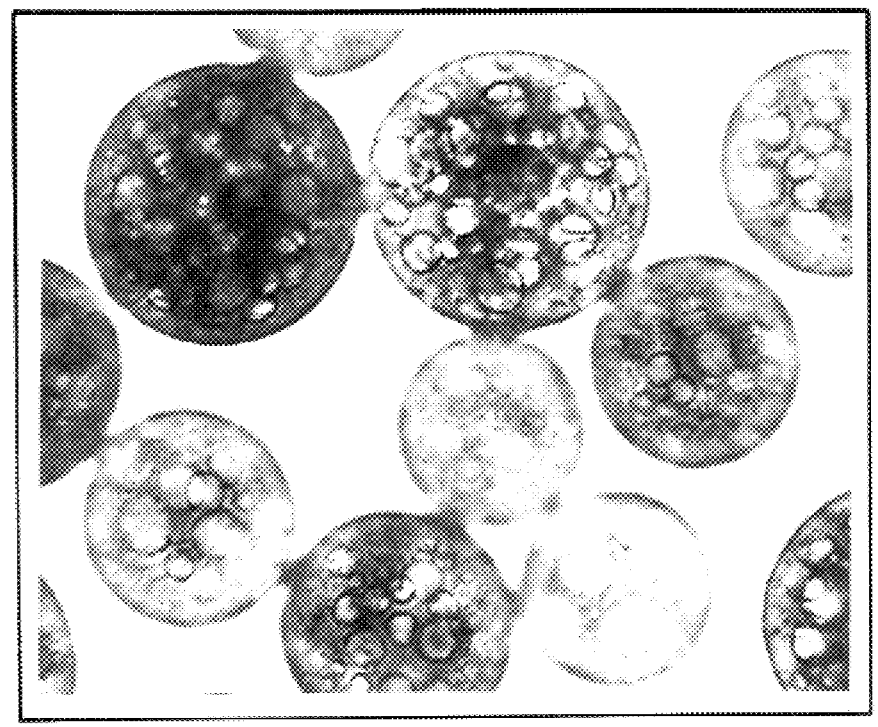
FIG. 9B is a phase contrast micrograph of a typical preparation of microspheres showing internal structure magnified 400 times.

Results:

Encapsulation: The encapsulation procedure as described in the methods section consistently yielded large microspheres with an average size of 75 to 100 microns. An example from a typical preparation is shown in FIG. 9 and in Table IV.

Figure 10:
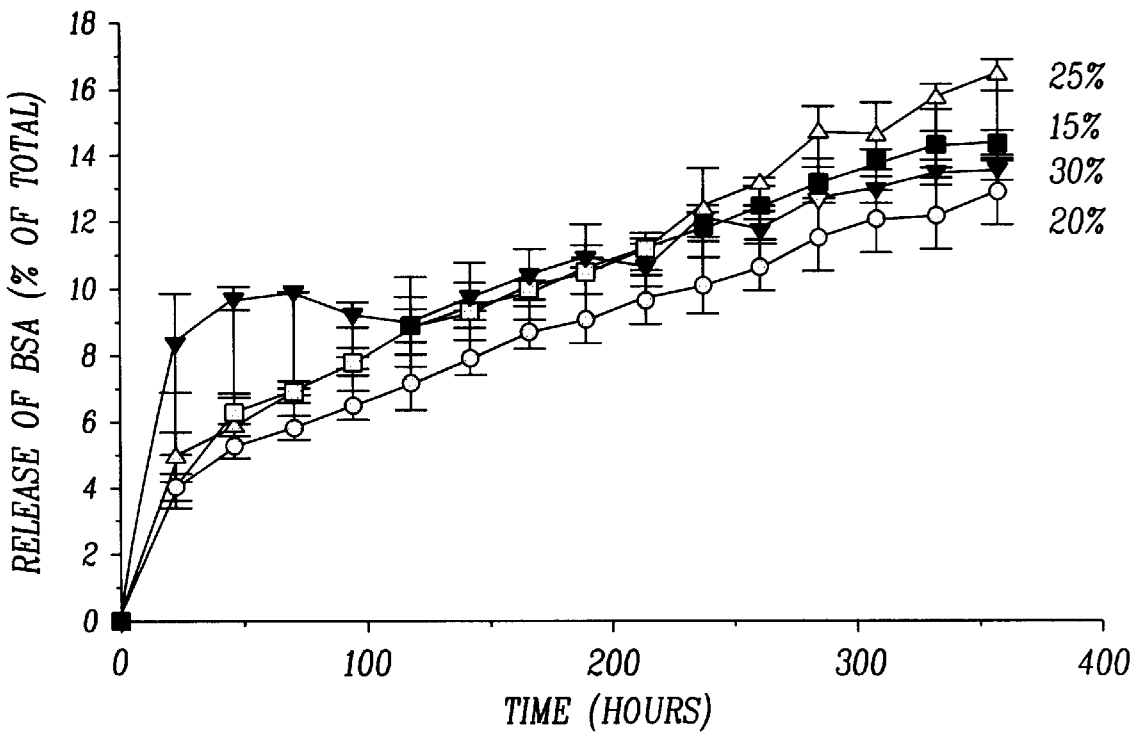
FIG. 10 is graph showing that the initial density (w/v) of PLGA in BSA-microspheres had little effect on the release rate of BSA when 50 µl of 200 mg per ml BSA was encapsulated in PLGA solutions at the indicated densities.
Figure 11:
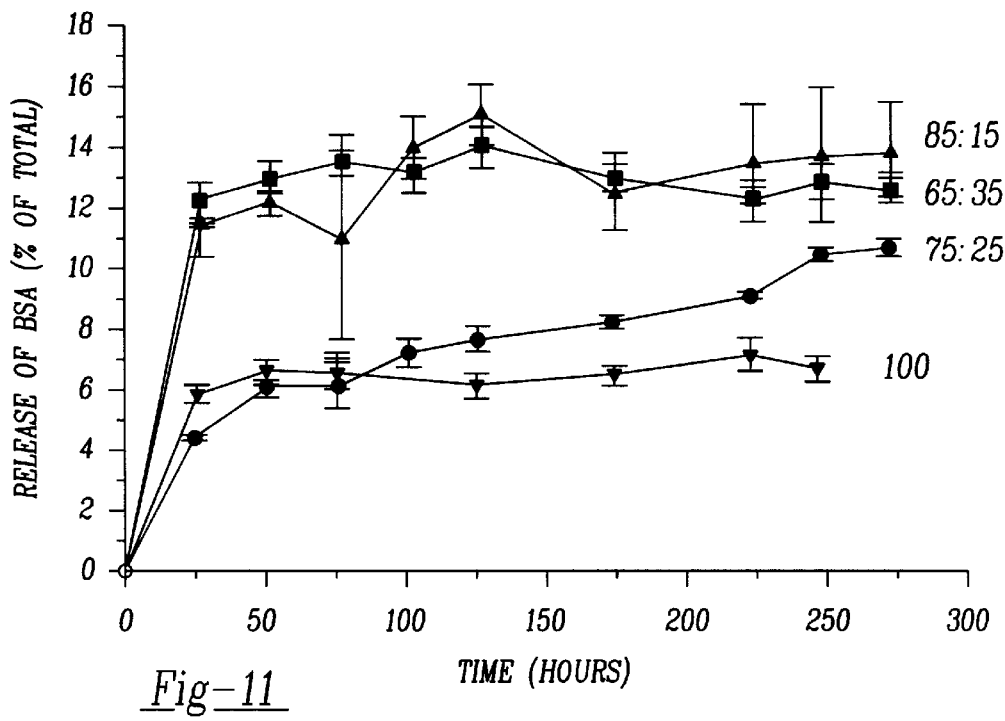
FIG. 11 is a graph showing that the release of BSA from PLGA microspheres did not consistently correlate with PLGA copolymer composition, the corresponding ratios of lactide to glycolide being shown on the right hand side of the Figure, the data presented in the Figure being the average +/- s.e of triplicate data points.

BSA Release from PLGA microspheres: In BSA encapsulation experiments (no virus included), a number of different parameters in the encapsulation procedure were tested. Specifically, the effect of varying the initial concentration of PLGA and the composition of the PLGA copolymer was examined. As seen in FIG. 10, the starting density had little effect on BSA release, with all preparations releasing approximately equal amounts of protein over the course of the experiment. Further, no consistent correlation between polymer composition and protein release was detected (FIG. 11). It is hypothesized that variations in polymer density and composition have little effect on the release of molecules from such a large sphere matrix. Therefore, for subsequent viral encapsulations, a 15% (w/v) 75:25 PLGA and followed the procedure described above.

Figure 12:
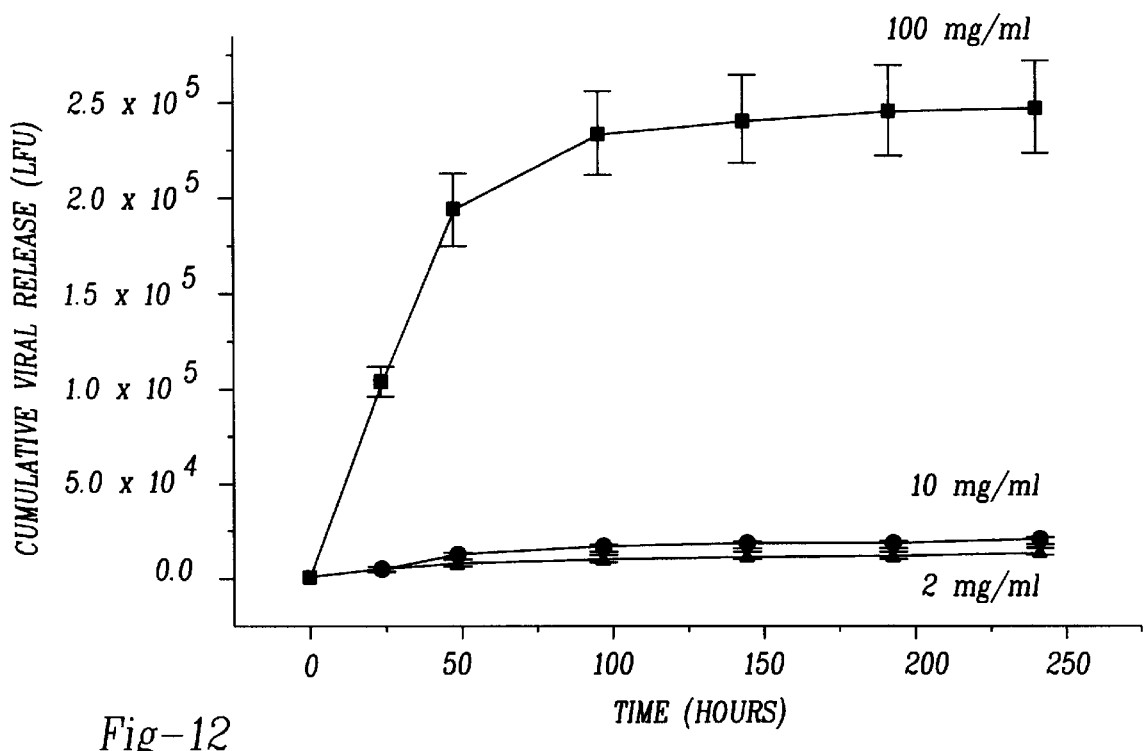
FIG. 12 is a graph showing the cumulative release of Ad.RSVlacZ from PLGA microspheres as a function of BSA concentration in the viral encapsulation buffer. BSA was included in the viral encapsulation buffer at the indicated concentrations.

Viral release from PLGA microspheres: The use of organic solvents with biological substrates, such as adenoviruses, often necessitated the inclusion of a protective agent. This protective agent prevented the denaturation of the viral coat and fiber proteins at the organic interface. The protective effect of a number of different compounds, including glycerol, sucrose, and protein was assessed. Striking results were found with high concentrations of BSA (FIG. 12). In these experiments, acetylated BSA (Sigma) was added to Ad.RSVntlacZ solutions prior to the encapsulation procedure. After synthesis of the spheres, the release of virus was determined over a ten day time course. The inclusion of high concentrations (100 mg/ml) of BSA dramatically increased the release rate and total amount of virus released compared with lower concentrations of BSA (2 and 10 mg/ml, see Table II). BSA concentrations greater than 100 mg/ml showed no significant improvement in release kinetics (data not shown).

Figure 13:
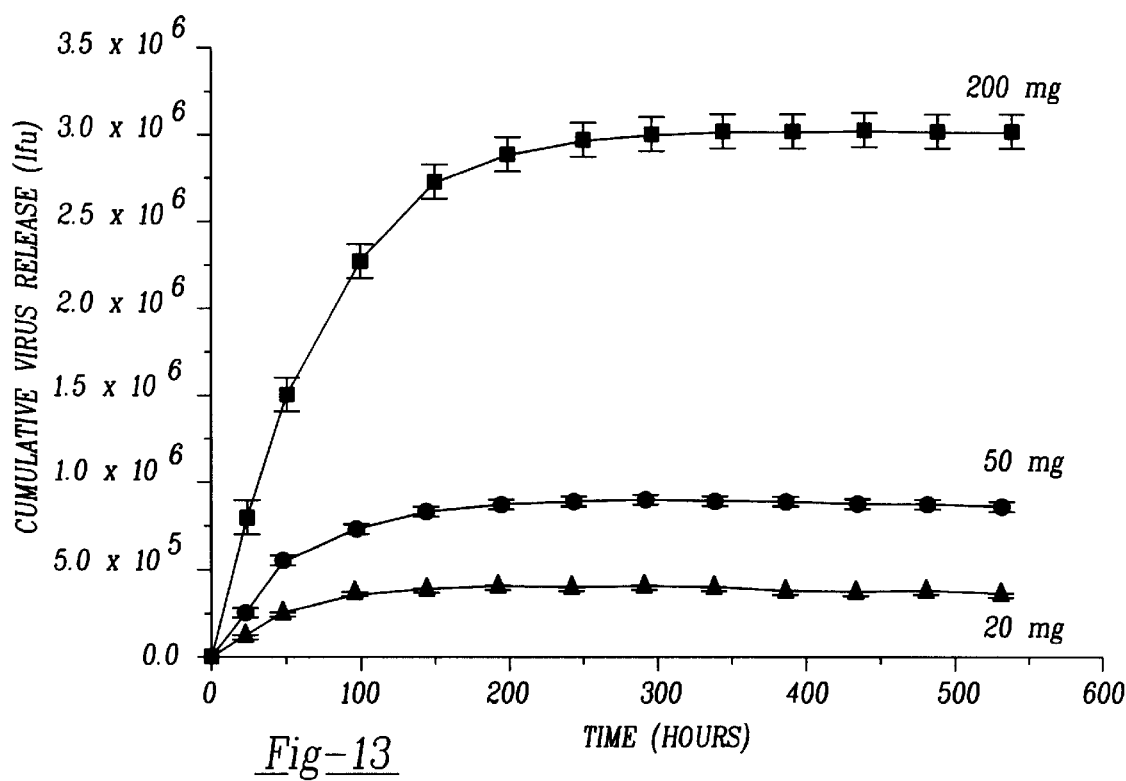
FIG. 13 is a graph showing the dose response assay for release of Ad.RSVntlacZ from PLGA microspheres.
Figure 14:
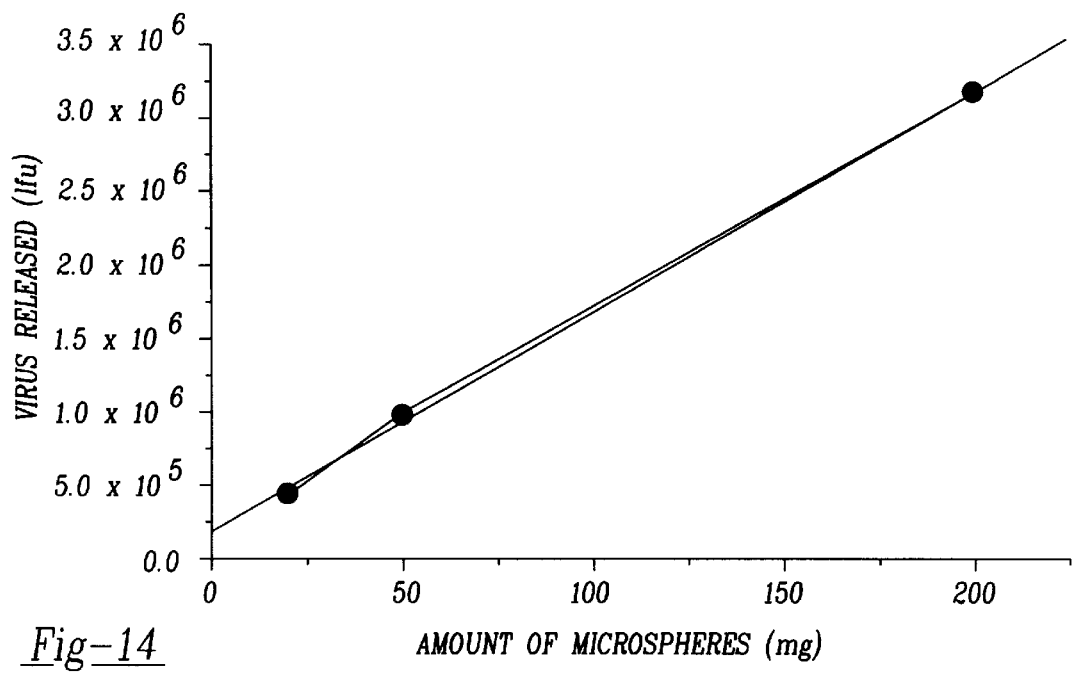
FIG. 14 is a graph showing a regression analysis of viral release as a function of the amount of microspheres.
Figure 15:
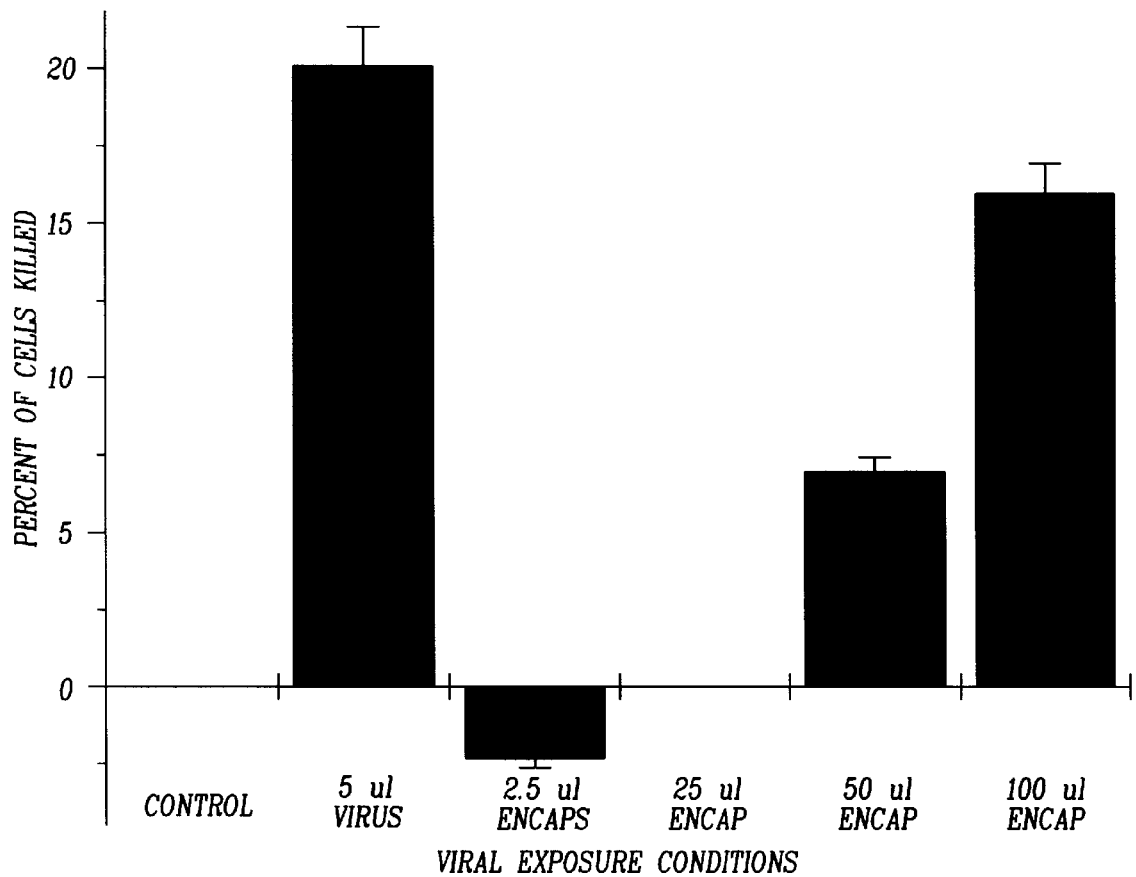
FIG. 15 is a graph showing the dose response of release of Ad.RSVtk with increasing volumes of viral microspheres.

In a dose response experiment (FIG. 13), it was found that over a 22 day time course, $3.11\pm0.09\times10^6$ lfu were released from 200 mg of viral-microsphieres. Regression analysis revealed a linear correlation (p=0.018 and r=0.999) between viral release and the amount of microspheres (FIG. 14). Further, a dose response study using encapsulated Ad.RSVtk demonstrated that increasing amounts of encapsulated Ad.RSVtk led to increased killing of 9L cells after a 10 day exposure followed by incubation with 1 $\mu$M GCV (FIG. 15).

Ganciclovir encapsulation and release: Current protocols employ the systemic administration of GCV to experimental tumors treated with AdRSVtk. Perez-Cruet et al. showed that with systemic doses of GCV above 80 mg/kg it was possible to eradicate tumors in a rat model similar to the present invention following even a single dose of Ad.RSVtk (Perez-Cruet et al., 1994). The high toxicity of systemic GCV, however, limits the dose which can be given in humans (15 mg/kg), and, thereby reduces efficacy. Hence, it would appear that if the local concentration of GCV could be increased to the level achieved by Perez-Cruet et al., then treatment with virus would be more efficacious. Furthermore, if the dose could be delivered intratumorally then systemic toxicity could be avoided. PLGA encapsulation would allow for the local delivery of both virus and high concentrations of GCV augmenting therapy.

Previous investigations evaluated intrathecal administration of GCV for tk-mediated cell killing (Ram et al, 1994). While these studies showed little CNS toxicity for this form of therapy, they also showed poor efficacy with treatment compared to systemically administered GCV. However, when utilizing the intrathecal route of administration for pharmaceutical agents, the dynamics of CSF flow must be taken into consideration. Antimicrobials administered into the CSF have been shown to attain different levels in various regions of the CNS depending on the location where such agents are introduced (Kaiser and McGee, 1975). A homogeneous equilibrium of drug levels does not occur within the CSF. On the other hand, delivering agents directly to the desired location of action has been done effectively with chemotherapeutic agents (Brem et al., 1994, Judy et al, 1995, Walter et al., 1994), which circumvents the effect of CSF regional concentration gradients. In this way, encapsulated GCV could be delivered directly to the tumor bed affording a high local sustained concentration of prodrug improving efficacy.

To initially evaluate the kinetics of GCV encapsulation and release in vitro, GCV-microspheres were synthesized as described for synthesis of adenoviral-PLGA microspheres. Fifty $\mu$l of a 3.65 mg/ml solution of GCV was encapsulated in PLGA and the resulting microspheres were freeze-dried overnight. The encapsulation efficiency was 34.2% and the % core loading was 0.125% (Table III). To measure release of drug, 50 mg of GCV-microspheres were incubated at 37° C. in 1 ml of 50 mM potassium phosphate buffer (pH=6.8). The solution was agitated during the incubation. Aliquots were removed daily and assayed using HPLC. Brilfly, 100 $\mu$l samples and GCV standards were directly injected into a 125×4 mm LiChrosphere 100 RP-18 5 uM reverse phase column (Merck). The mobile phase was a 1:99 mixture of acetonitrile and ammonium phosphate, pH=6.8. At a flow rate of 1 ml/min, GCV had a retention time of approximately 5.0 minutes.

Figure 16:
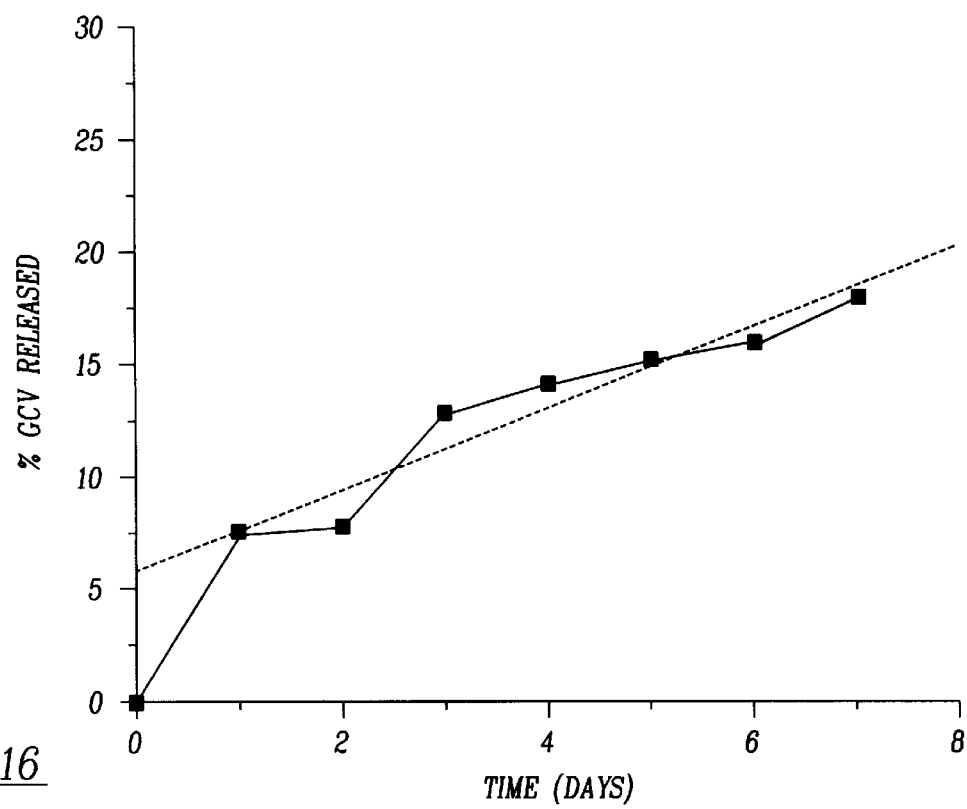
FIG. 16 is graph showing the release of GCV from PLGA microspheres.

As seen in FIG. 16, 50 mg of GCV-microspheres released nearly 12 ug of GCV or approximately 19% of the total amount of encapsulated drug over 7 days. There was an initial burst of drug comprising 7.8% of the total or 4.88 ug GCV. Thereafter, a linear release (r=0.962, p<0.001) of drug was noted.

A rough estimate of the amount of expected GCV release in vivo can be calculated. If 50 mg of GCV-microspheres are administered to a 100 $mm^3$ tumor (total tumor volume of 0.1 ml), and also assuming the drug, when released, is evenly distributed throughout the tumor mass, the first day release of GCV would be 48.8 $\mu$g/ml or 176 $\mu$M. This value is well above the $IC_{50}$ values reported for many types of cell lines expressing HSV-tk (Maron et al., 1995, Smythe et al., 1994). While these calculations don't take into account diffusion of the GCV into the surrounding tissue, from these data, it seems very likely that delivery of encapsulated GCV will result in high local levels of GCG, thereby avoiding the toxicity of systemic delivery.

Experimental Section IV

Introduction:

The following experiments provide an animal model for inflammatory bowel disease and in vivo use of the present invention therewith. The experiment addresses the issue of defining the target tissue, because the biology of the cell, the number of cells, and the environments of the cell predict the type of gene transfer vector and its administration. Additionally, the experiments define what gene product to express. This issue takes into account the ability of the gene product to inhibit the initiation or progress of the disease, and in this case, specifically inflammatory bowel disease (IBD).

Animal Models of IBD:

The availability of animal models of IBL), such as IL-10 knockout mice (IL-10T mice) (Kuhn, et al., 1993), IL-2 deficient mice (Sadlack et al., 1993), and the T-cell receptor knockout mouse (Mombaerts et al., 1993), enable the determination of whether gene replacement can inhibit the onset or progression of disease. In the IL-10 knockout model, disease is present in weakling mice which progresses with age. The onset of the disease can be blocked by systemic administration of recombinant IL-10 protein (Kuhn et al., 1993). However, recombinant protein therapy in adults with disease was not effective. These results may be due in part to the short half life of recombinant IL-10 protein (less than one hour at 37° C.).

A recombinant adenoviral vector expressing human IL-10, was developed to test the paradigm that gene replacement strategies may inhibit the development and ameliorate established IBD in this model. AdRSVIL-10 contains the human IL-10 cDNA expressed from the RSV LTR in an adenovirus type 5 backbone. The liver was chosen as a target tissue in these initial studies because it can be easily infected with viral vectors following intravenous injection (i.v.).

When treated intravenously with 10 μg of LPS, IL-10T mice, but not normal mice, succumbed to endotoxic shock (Berg et al., 1995). Previous studies have also shown that these mice are protected by a bolus injection of IL-10 (10 μg) 30 minutes prior to injection (Berg et al., 1995). The bioactivity of the virus was tested using the same LPS challenge. Mice were infected by tail vein injection with $5 \times 10^8$ infectious particles of AdRSVIL,-10 (n=6) or $5 \times 10^8$ infectious units of a control virus, AdRSVlacZ (n=7). Human IL-10 levels in the serum of all treated IL-10T mice was measured at day 6.

The range of human IL-10 was from 96.1 pg/ml to 269.6 pg/ml in the AdRSVIL-10 injected animals. AdRSVlacZ injected animals had less than 80 pg/ml of cross reacting material. Ten micrograms of LPS was injected i.v. into all mice on day 9 and survival monitored over the next 72 hours. As shown in Table V, all IL-10T mice injected with AdRSVlacZ succumbed. Two of the mice injected with AdRSVIL-10 died. These two mice had 96.1 and 133.9 pg/ml circulating IL-10 while the concentration of IL-10 in the surviving AdRSVIL-10 treated animals was greater than 200 pg/ml. These same animals were able to withstand a second LPS challenge 11 days later (20 days after AdRSVIL-10 injection).

TABLE V

| Treatment[a] | [IL-10][b] | Effect[c] |
|---|---|---|
| AdRSVlacZ | 53.8 ± 29.6 (N = 7) | Died |
| AdRSVIL-10 | 115 ± 18.9 (n = 2) | Died |
| AdRSVIL-10 | 233.2 ± 24.8 (n = 4) | Survived |

[a]$5 \times 10^8$ 08 infectious units were injected i.v.
[b]Concentration of IL-10 in serum in pg/ml 6 days post injection.
[c]Effect following LPS challenge.

Figure 17:
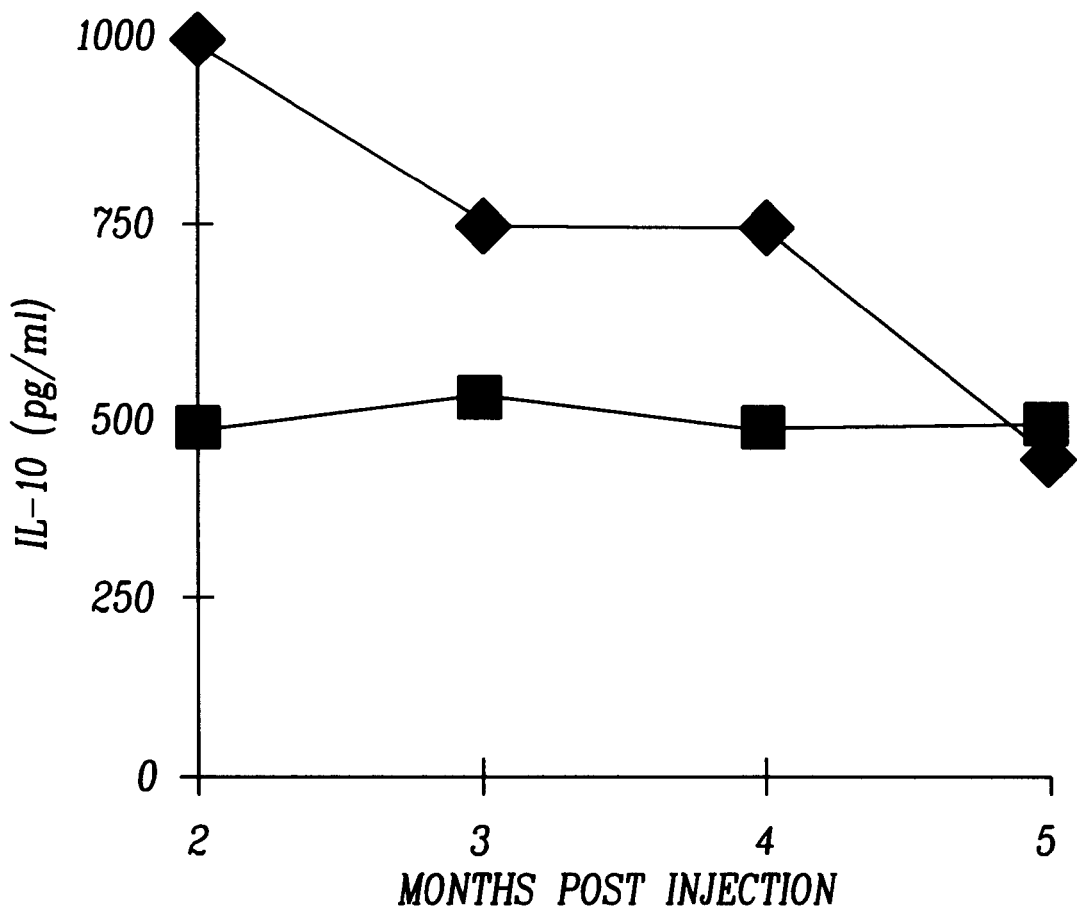
FIG. 17 is a graph showing the injection of AdRSVIL-10 in immunocompetent CBA mice resulting in prolonged expression of IL-10 in vivo.

It appears that the inherent immunosuppressive properties of IL-10 are likely to result in prolonged gene expression in liver. To test this hypothesis, AdRSVIL-10 was injected into CBA mice, and the expression of IL-10 was monitored over time. The robust immune response to Ad by CBA mice generally results in a rapid decline in gene expression following adenovirally mediated gene transfer to liver (Humpheries et al., 1987, Barr et al., 1995). However, IL-10 expression following AdRSVIL-10 injection has persisted for greater than five months and remains stable at this time at 200 pg/ml (FIG. 17). Long term expression of other anti-inflammatory cytokines may also have an effect on the initiation and/or progression of disease in this model of IBD.

Conclusions

Recombinant adenoviruses are capable of expressing significant levels of IL-10 in an animal model of inflammatory bowel disease. The level of IL-10 was sufficient to protect IL-10 to knockout mice from endotoxic shock following LPS administration. Further, expression of IL-10 following adenoviral mediated gene transfer to liver was prolonged relative to other transgenes. Thus, the use of adenoviral vectors to achieve pharmacologically relevant levels of gene products to alter the natural history of IBD) is feasible.

Throughout this application various publications are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, the invention may be practiced otherwise than as specifically described.

TABLE II

The effect of BSA concentration on the release of Ad.RSVntlacZ from PLGA microspheres. Data are from the experiment in FIG. 9.

| BSA concentration (mg/ml) | Total released virus (lfu) | Fold increase |
|---|---|---|
| 2 | $1.0 \times 10^4$ | 1 |
| 10 | $1.81 \times 10^4$ | 1.81 |
| 100 | $2.46 \times 10^5$ | 24.6 |

TABLE III

| GCV loading of microspheres | |
|---|---|
| encapsulation efficiency $\frac{(\text{encap GVC})}{(\text{total GCV})} \times 100$ | 34.2% |
| % core loading $\frac{(\text{mg of drug})}{(\text{mg of spheres})} \times 100$ | 0.125% |
| total μg of GCV in orporated in 50 mg of microspheres | 64.2 μg |

TABLE IV

| Viral Encapsulation and Release from PLGA microspheres | |
|---|---|
| starting material LFU | $3.0 \pm 0.15 \times 10^8$ |
| unencapsulated virus in wash (% of starting LFU) | $3.7 \pm 0.14 \times 10^7$ (12.3%) |
| Total virus released in 12 days (% of starting LFU) | $3.0 \pm 0.12 \times 10^6$ lfu (1.0%) |

What is claimed is:

1. A controlled release delivery system comprising:
   a functional gene vector; and
   a biodegradable polymer microsphere encapsulating said vector, said microsphere consisting essentially of a biodegradable polymeric coating wherein said system includes a drug selected from the group consisting of ganciclovir, 5-flurocytosine, and 6-thioxanhine.

2. A delivery system as set forth in claim 1 wherein said microsphere consists of an enteric coating made of a polymer.

3. A delivery system as set forth in claim 1 wherein said microsphere consists essentially of a polymer or copolymer selected from the group consisting of poly(lactic-glycolic acid) polyester, cellulose acetate phthalate, hydroxypropylmethyl cellulose phthalate poly(butyl methacrylate), (2-dimethyl aminoethyl) methacrylate, and methyl methacrylate.

4. A delivery system as set forth in claim 1 where said microspheres have a size between about one to 150 microns.

5. A delivery system as set forth in claim 1 where said system further comprises a drug which is coactive with said vector.

6. A method of making a controlled release delivery system by encapsulating a functional gene vector in a biologically degradable polymeric microsphere by mixing an acidic hydrophobic solvent with a pH of 2–4 with the primary suspension of an aqueous solution, polymer solution, and an emulsifier to assist extraction of the microspheres and evaporation of the first mentioned aqueous solution.

7. A method as set forth in claim 6 wherein said encapsulating step is further defined as adding the functional gene vector to a polymer solution and first forming a water-oil emulsion and, then forming a water-oil-water emulsion of microspheres encapsulating the gene vector and then separating the formed microspheres form the emulsion.

8. A method as set forth in claim 7 further including the step of forming an aqueous solution containing the functional gene vector and an aqueous solvent and adding the aqueous solution to the polymer solution.

9. A method as set forth in claim 8 wherein said first forming step is further defined as gently mixing the aqueous solution, polymer solution, and an emulsifier to form a primary suspension including microspheres of the polymer encapsulating functional gene vector.

10. A method as set forth in claim 9 where said step of forming a water-oil-water emulsifier is further defined as mixing an acidic hydrophilic solvent with the primary suspension to assist extraction of the microspheres and evaporation of the first mentioned aqueous solvent.

11. A method as set forth in claim 10 where the acidic hydrophilic solvent is selected from the group consisting of polyvinylalcohol, isopropanol, water.

12. A method as set forth in claim 9 wherein said step of forming a water-oil-water emulsifier is further defined as mixing a hydrophilic solvent with the primary suspension to assist extraction of the microspheres and evaporation of the first mentioned aqueous solvent.

13. A method as set forth in claim 7 further including the step of forming an aqueous solution containing the functional gene vector and an aqueous solvent containing an encapsulation stabilizer and adding the aqueous solution to the polymer.

* * * * *